United States Patent
Özyigit et al.

(10) Patent No.: US 11,942,201 B2
(45) Date of Patent: Mar. 26, 2024

(54) VALIDATION METHOD AND VALIDATION APPARATUS FOR SEALED UNIT

(71) Applicants: Ali Özyigit, Bonn (DE); Baris Cem Sal, Bonn (DE)

(72) Inventors: Ali Özyigit, Bonn (DE); Baris Cem Sal, Bonn (DE)

(73) Assignee: DEUTSCHE POST AG, Bonn (DE)

( * ) Notice: Subject to any disclaimer, the term of this patent is extended or adjusted under 35 U.S.C. 154(b) by 108 days.

(21) Appl. No.: 17/235,604

(22) Filed: Apr. 20, 2021

(65) Prior Publication Data

US 2021/0327046 A1    Oct. 21, 2021

(30) Foreign Application Priority Data

Apr. 21, 2020 (EP) .................................... 20170522

(51) Int. Cl.

| | |
|---|---|
| *G06T 7/00* | (2017.01) |
| *G06V 10/141* | (2022.01) |
| *G06V 10/40* | (2022.01) |
| *G06V 20/66* | (2022.01) |
| *G06V 20/80* | (2022.01) |
| *G16H 20/13* | (2018.01) |

(52) U.S. Cl.
CPC ............ *G16H 20/13* (2018.01); *G06T 7/0004* (2013.01); *G06V 10/141* (2022.01); *G06V 10/40* (2022.01); *G06V 20/66* (2022.01); *G06V 20/80* (2022.01); *G06T 2207/30108* (2013.01)

(58) Field of Classification Search
CPC ........ G06T 7/0004; G06T 2207/30108; G06V 20/00; G06V 30/10; G06V 10/141; G06V 10/40; G06V 20/66; G06V 20/80; G16H 20/13; G06F 16/901; G06F 16/90344; B65B 57/10; G06K 17/0029
USPC .................................................. 382/143, 100
See application file for complete search history.

(56) References Cited

U.S. PATENT DOCUMENTS

| | | | |
|---|---|---|---|
| 9,298,997 B1 * | 3/2016 | Lecky | G06V 10/245 |
| 9,969,571 B1 * | 5/2018 | Lehmann | B65G 57/03 |
| 10,593,425 B1 * | 3/2020 | Truscott | G16H 20/13 |
| 2003/0219145 A1 | 11/2003 | Smith | |
| 2007/0086626 A1 | 4/2007 | Mariani et al. | |
| 2008/0000979 A1 * | 1/2008 | Poisner | G16H 20/13 |
| | | | 235/462.01 |
| 2011/0186629 A1 | 8/2011 | Stuck et al. | |
| 2013/0289494 A1 | 10/2013 | Artsyukhovich et al. | |

(Continued)

*Primary Examiner* — Sheela C Chawan
(74) *Attorney, Agent, or Firm* — Reinhart Boerner Van Deuren P.C.

(57) ABSTRACT

An apparatus to perform or control obtaining or causing obtaining an image of at least a part of a surface of a sealed unit. The apparatus derives or causes to derive a representation of the at least a part of the surface from the image. The representation includes a set of values representing height levels of corresponding sections of the part of the surface. The apparatus generates or causes generating a string of characters based on the representation of the part of the surface. The string of characters includes a first portion representative of the set of height levels and a second portion generated based on a function of the representation and/or of the first portion of the string of characters. The apparatus associates or causes associating information representing the string of characters with identification information of the sealed unit.

23 Claims, 6 Drawing Sheets

(56) References Cited

U.S. PATENT DOCUMENTS

| | | | |
|---|---|---|---|
| 2014/0175165 A1* | 6/2014 | Havens | G06Q 30/0185 |
| | | | 235/375 |
| 2016/0239795 A1* | 8/2016 | Burch, V | G06Q 10/087 |
| 2017/0305589 A1* | 10/2017 | Yuyama | G06Q 20/4014 |
| 2017/0352015 A1 | 12/2017 | Xu et al. | |
| 2018/0046776 A1* | 2/2018 | Chalifoux | G16H 20/13 |
| 2018/0060657 A1* | 3/2018 | Stuck | G06K 7/1417 |
| 2019/0342102 A1* | 11/2019 | Hao | H04L 9/3247 |

* cited by examiner

VALIDATION METHOD AND VALIDATION APPARATUS FOR SEALED UNIT

CROSS-REFERENCE TO RELATED PATENT APPLICATIONS

This patent application claims priority to European Patent Application No. 20170522.5, filed Apr. 21, 2020, the entire teachings and disclosures of which are incorporated herein by reference thereto.

FIELD OF THE DISCLOSURE

The present disclosure relates in general to the field of validation and verification of sealed units, in particular to validation and verification of sealed drug packages, sealed consignment units, sealed bottles and/or sealed packages for tobacco and/or nicotine based products.

BACKGROUND

Counterfeiting of drugs and medication has become a considerable problem. Counterfeit medication or counterfeit drug usually refers to a pharmaceutical product which is produced and sold with the intent that the counterfeit drug or medication has the appearance of a genuine counterpart and thus deceptively appears alike as regards origin or effectiveness. A counterfeit drug may contain inappropriate quantities of active ingredients, or none, and may thus be improperly processed within the body (e.g., absorption by the body), may contain ingredients that are not on the label (which may or may not be harmful).

For example, identifiers may be employed for addressing this problem. Pharmaceutical products (e.g. sealed packages for packing the pharmaceutical products) are usually provided with an identifier such as a serial number which may be provided on a sealable unit such as a sealable package. Such identifier may then be linked to identification information of the pharmaceutical product such as the product's origin, a batch number, and/or an expiration date, e.g. in a corresponding database. Being provided with such identifier, a pharmaceutical product may be tracked and its location can be traced in particular during important stages of its lifecycle. Similar issues exist in case of sealed bottles in particular for alcoholic beverages and/or in case of sealed packages for tobacco and/or nicotine based products which are often subject to counterfeiting.

SUMMARY OF SOME EXAMPLE EMBODIMENTS OF THE INVENTION

It is inter alia an object of the invention to provide in particular methods, apparatuses, systems and computer programs improving identification and verification of sealed units such as sealed packages, in particular sealed drug packages, sealed consignment units, sealed bottles and/or sealed packages for tobacco and/or nicotine based products. A further object of the invention is to provide methods, apparatuses, systems and computer programs enabling determination of whether or not a seal of a sealed unit has been opened and/or illegally manipulated.

According to a first exemplary aspect of the invention, a method performed by at least one first apparatus is disclosed, the method comprising obtaining or causing obtaining an image of at least a part of a surface of a sealed unit; deriving or causing deriving a representation of the at least a part of the surface from the image, the representation comprising a set of values respectively representing a corresponding set of height levels of corresponding sections of the at least a part of the surface; generating or causing generating a string of characters based on the representation of the at least a part of the surface, the string of characters comprising at least a first portion representative of the set of height levels of the corresponding sections of the at least a part of the surface and a second portion generated based on a function of the representation and/or of the first portion of the string of characters; and associating or causing associating information representing the string of characters with identification information of the sealed unit.

The method according to the first aspect of the invention may for instance be performed by an apparatus or by a system that comprises a plurality of apparatuses. The apparatus or system may for instance form a part of a device for registering a sealed unit with corresponding identification information of the sealed unit. The apparatus or system may further correspond to or be incorporated in a mobile device used in connection with such device.

According to a second exemplary aspect of the invention, a method performed by at least one second apparatus is disclosed, the method comprising obtaining or causing obtaining first information representing a first string of characters with a first portion representative of a set of height levels of corresponding sections of at least a part of a surface of a first sealed unit; determining or causing determining, based on the obtained first information, whether or not the first string of characters is present in a database; and if the first string of characters is present in the database: outputting or causing outputting confirmation information.

The method according to the second aspect of the invention may for instance be performed by an apparatus or by a system that comprises a plurality of apparatuses. The apparatus or system may for instance correspond to or be comprised by a mobile device, e.g. a smartphone, by a device for verification of a sealed unit, and/or by a network server and/or a network server cloud.

For all aspects of the invention presented above (referred to as the "respective aspect" below), the following is disclosed:

A computer program according to the respective aspect of the invention, the computer program when executed by a processor causing an apparatus or system to perform or control the method according to the respective aspect of the invention.

A computer readable storage medium according to the respective aspect of the invention, in which the computer program according to the respective aspect of the invention is stored. The computer readable storage medium could for example be a disk or a memory or the like. It may for instance be tangible and/or non-transitory. The computer program could be stored in the computer readable storage medium in the form of instructions encoding the computer-readable storage medium. The computer readable storage medium may be intended for taking part in the operation of a device, like an internal or external memory (e.g. a Read-Only Memory (ROM)) or hard disk of a computer, or be intended for distribution of the program, like an optical disc.

An apparatus according to the respective aspect of the invention, which is configured to perform or comprises respective means for performing or controlling the method according to the respective aspect of the invention. The means of the apparatus can be implemented in hardware and/or software. They may comprise for instance at least one processor for executing computer program code for performing the required functions, at least one memory storing the program code, or both. Alternatively, they could comprise for instance circuitry that is designed to implement the required functions, for instance implemented in a chipset or a chip, like an integrated circuit. In general, the means may comprise for instance one or more processing means.

An apparatus according to the respective aspect of the invention, comprising at least one processor and at least one memory including computer program code, the at least one memory and the computer program code configured to, with the at least one processor, cause an apparatus (e.g. the apparatus according to the respective aspect of the invention) at least to perform or control the method according to the respective aspect of the invention.

A system according to the respective aspect of the invention, the system comprising a plurality of apparatuses and configured to perform or comprises respective means for performing or controlling the method according to the respective aspect of the invention.

The disclosed apparatus according to any aspect of the invention may be a module or a component for a device, for example a chip and/or processor. Alternatively, the disclosed apparatus according to any aspect of the invention may be a device, for instance a server or other electronic device. The disclosed apparatus according to any aspect of the invention may comprise only the disclosed components (e.g. means) or may further comprise one or more additional components.

Furthermore, according to a third aspect of the invention, a system is disclosed, the system comprising an apparatus or system according to the first aspect of the invention and an apparatus or system according to the second aspect of the invention.

In other words, a system is disclosed that may comprise:
at least one first apparatus configured for:
  obtaining or causing obtaining an image of at least a part of a surface of a first sealed unit;
  deriving or causing deriving a representation of the at least a part of the surface from the image, the representation comprising a set of values respectively representing a corresponding set of height levels of corresponding sections of the at least a part of the surface;
  generating or causing generating a first string of characters based on the representation of the at least a part of the surface, the first string of characters comprising at least a first portion representative of the set of height levels of the corresponding sections of the at least a part of the surface and a second portion generated based on a function of the representation and/or of the first portion of the string of characters; and
  associating or causing associating first information representing the first string of characters with identification information of the first sealed unit; and
at least one second apparatus configured for:
  obtaining or causing obtaining the first information representing the first string of characters with a first portion representative of a set of height levels of corresponding sections of the at least a part of the surface of the first sealed unit;
  determining or causing determining, based on the obtained information, whether or not the first string of characters is present in a database; and
  if the first string of characters is present in the database:
    outputting or causing outputting confirmation information.

One or more of the features and/or embodiments disclosed in the following may further define the first and/or second aspect of the invention.

In accordance with aspects of the present invention, information derived from an image of a part of a surface of a sealed unit that represents a surface structure, in particular a microstructure, is employed on the one hand for uniquely identifying the sealed unit and on the other hand for verifying that the sealed unit is not counterfeit and/or that a seal of the sealed unit has not been opened. To this end, the information derived from the image is associated with identification information of the sealed unit e.g. at a registering stage employing the method according to the first aspect. At a later stage, e.g. when validity of the sealed unit is to be verified, presence of the information representative of the surface structure in a database is verified employing a method according to the second aspect.

Thereby, employing a method according to the first aspect, a string of characters, e.g. a code, is generated that includes a first portion representative of height levels of sections of a part of a surface of a sealed unit. In an exemplary embodiment of the first and the second aspect, the surface of the sealed unit at least in part corresponds to or comprises a bare surface portion of the sealed unit, at least a part of a label of the sealed unit and/or at least a part of a seal for sealing the sealed unit.

Further, in an exemplary embodiment, the height levels of the sections are representative of a microstructure of the surface of the sealed unit. Such structure of the surface of the sealed unit, e.g. the microstructure, is a unique feature of the particular surface and can therefore be advantageously employed for uniquely identifying the sealed unit. For example, in case a sealed unit corresponds to or comprises a sealed carton box including one or more blisters for a certain type of pills, while a surface of the sealed carton box may appear equal to a corresponding surface of a further carton box for the same type of pills macroscopically, these surfaces are different on a microscopic level. In analogy to a human fingerprint such microstructure of a surface of such box may thus be used for uniquely identifying the box.

While it is possible to use an image of the surface structure for identifying such surface, employing a method according to the first aspect, a string of characters is generated based on the image that uniquely represents the surface and thus the sealed unit. Use of the string of characters instead of the image provides a considerable advantage in that a considerably larger number of sealed units can be processed in a given time. At the same time, by uniquely reflecting the surface structure of the sealed unit, use of the string of characters provides a highly secure means for reliably identifying and verifying a sealed unit.

For example, when a sealed unit such as a sealed package is produced, an image can be taken of at least a part of a surface thereof, a string of characters can be generated from the image and the string of characters may be associated with identification information of the sealed package.

As mentioned above, pharmaceutical products (e.g. sealed packages for packing the pharmaceutical products) are usually provided with an identifier linked to identification information of the pharmaceutical product such as the product's origin, a batch number, and/or an expiration date, e.g. in a corresponding database. In aspects of the present disclosure, the string of characters generated based on the representation of the at least a part of the surface may replace or supplement such identifier. In other words, in an exemplary embodiment the sealed unit corresponds to or comprises a sealed package for one or more pharmaceutical products and/or medical tools. In the exemplary embodiment, the identification information corresponds to or comprises a serial number, an origin of the pharmaceutical product and/or the medical tool, a batch number of the pharmaceutical product and/or the medical tool, a type of the pharmaceutical product and/or the medical tool, an identification number and/or code of the pharmaceutical product and/or the medical tool, a name of the pharmaceutical product and/or the medical tool, an expiration date of the pharmaceutical product, and/or information identifying an addressee of the pharmaceutical product and/or the medical tool, e.g. a name of the addressee, a place of birth of the addressee, date of birth of the addressee and/or residence of the addressee. By associating such identification information with the string of characters, the string of characters can be employed for similar purposes as the mentioned identifier, in particular for identifying, tracing and tracking of the corresponding sealed unit.

Thus, on the one hand, by associating identification information of non-counterfeit, genuine, sealed units with corresponding strings of characters identifying the respective sealed units, e.g. by storing identification information in association with corresponding strings of characters in a database, it becomes possible to recognize counterfeit sealed units. Namely, obtaining a string of characters based on a surface of a counterfeit sealed unit will yield a string of characters not associated with any identification information, in particular not stored in a database. Therefore, if employing a method according to the second aspect, a string of characters is determined to be present in a database, it can be assumed with a high probability that the sealed unit is not counterfeit.

On the other hand, in case the image is taken of a part of the surface of the sealed unit at least in part corresponding to or comprising at least a part of a seal for sealing the sealed unit, it becomes possible, e.g. based on employing the method according to the second aspect, to determine that the seal has not been opened. If at a registering stage, an initial string of characters is generated based on a surface including at least part of a surface of the seal, a string of characters generated from a surface including the at least a part of the surface of the seal will differ from the initial string if this part of the surface of the seal has been damaged as a result of opening the seal after the registering stage. As a result, if based on employing a method in accordance with the second aspect, presence of said initial string of characters in a database is confirmed, it can be assumed with a high probability that the seal has not been opened (and e.g. potentially illegally repaired to appear non-opened).

While the methods according to the first and second aspects are applicable to packages for pharmaceutical products, in a further exemplary embodiment, the sealed unit corresponds to or comprises a sealed bottle in particular for an alcoholic beverage and/or a sealed package for a tobacco and/or nicotine based product. Thereby, in an exemplary embodiment, a tobacco and/or nicotine based product corresponds to or comprises loose tobacco, one or more cigarettes, one or more cigars, and/or e-cigarette liquid. Further, in an exemplary embodiment, a seal for sealing the sealed bottle and/or the sealed package for the tobacco and/or nicotine based product corresponds to or comprises a tax stamp.

In such case, a producer of such sealed unit may first acquire inactivated tax stamps which at a point in time of a corresponding production process of the sealed unit are activated, usually by or upon paying a corresponding tax. At this point in time, or upon acquiring the tax stamps, or at a different point in time before the sealed bottle and/or the sealed package for the tobacco and/or nicotine based product is sold, the method according to the first aspect may be carried out for registering the sealed bottle and/or the sealed package for the tobacco and/or nicotine based product in association with corresponding identification information.

In this way, by checking whether or not a corresponding string of characters is present in a database, activation, validity and/or authenticity of the tax stamp can be verified by employing the method according to the second aspect. In particular, reuse of a registered tax stamp can be prevented, if after having verified a tax stamp employing the method according to the second aspect, the associated information is removed from the database. The methods according to the first and the second aspect may thus advantageously be employed for preventing use and distribution of counterfeit tax stamps and corresponding counterfeit sealed bottles and/or sealed packages for tobacco and/or nicotine based products. It is noted that a method according to the second aspect may be performed for verifying activation, validity and/or authenticity of a tax stamp by tax authorities and/or by customers acquiring sealed bottles and/or sealed packages for tobacco and/or nicotine based products for resale from an original producer and/or by consumers (for example using a mobile device with a corresponding application installed thereon which may in particular be provided by a producer of the sealed unit).

In this exemplary embodiment, the identification information corresponds to or comprises information suitable for identifying the sealed bottle and/or the sealed package for the tobacco and/or nicotine based product, in particular a serial number, an origin of the sealed bottle and/or the sealed package for the tobacco and/or nicotine based product, a batch number of the sealed bottle and/or the sealed package for the tobacco and/or nicotine based product, a type of the sealed bottle and/or the sealed package for the tobacco and/or nicotine based product, an identification number and/or code of the sealed bottle and/or the sealed package for the tobacco and/or nicotine based product, a name of the sealed bottle and/or the sealed package for the tobacco and/or nicotine based product, an expiration date of the sealed bottle and/or the sealed package for the tobacco and/or nicotine based product, and/or information identifying an addressee of the sealed bottle and/or the sealed package for the tobacco and/or nicotine based product, e.g. name and address of a customer with the intention to resell the sealed bottle and/or the sealed package for the tobacco and/or nicotine based product. As in the case of the above disclose pharmaceutical product, it becomes possible not only to verify activation, validity and/or authenticity of a tax stamp, it becomes in addition possible to identify, trace and track a corresponding sealed bottle and/or the sealed package for the tobacco and/or nicotine based product.

It is noted that in particular in the exemplary embodiment in which the sealed unit corresponds to or comprises said sealed bottle and/or the sealed package for the tobacco and/or nicotine based product, in an exemplary embodiment, the method according to the first aspect and/or the method according to the second aspect comprises obtaining or causing obtaining an image of at least a part of a surface of a seal used for sealing the sealed bottle and/or the sealed package for the tobacco and/or nicotine based product.

In an exemplary embodiment, the at least one first apparatus is configured to obtain the identification information of the sealed unit from the sealed unit and/or via user input. For example, in an exemplary embodiment, the at least one first apparatus is configured to recognize (e.g. employing a camera and/or scanner comprised by or connected to the at least one first apparatus) text present on a surface of the sealed unit, e.g. employing optical character recognition (OCR) and/or is configured to recognize features present on a surface of the sealed unit via image recognition. Alternatively or in addition, in an exemplary embodiment, the at least one first apparatus is configured to derive the identification information of the sealed unit as electromagnetic, electric or magnetic type information employing one or more sensors comprised by or connected to the at least one first apparatus based on electromagnetic signals, electric or magnetic fields, e.g. RFID and/or NFC sensors. In other words, in an exemplary embodiment, the method according to the first aspect further comprises obtaining or causing obtaining the identification information of the sealed unit from the sealed unit and/or via user input.

The image obtained is in an exemplary embodiment a digital image for example acquired at or by the first apparatus with a digital camera or scanner comprised by or connected to the first apparatus. In an exemplary embodiment, the at least one first apparatus corresponds to or is comprised by a device comprising a digital camera or scanner and/or connected to a digital camera or scanner. The device may e.g. be installed at a facility at which the sealed unit is created, e.g. a facility of a pharmaceutical and/or medical device company or an authorized facility where the sealed unit may be registered. Further, in an exemplary embodiment, the at least one first apparatus may correspond to or be comprised by a mobile device. The mobile device may be used e.g. in a holder of the dedicated device and/or by authorized personnel, e.g. in the facility where the sealed unit is produced or at the authorized facility. Thereby, the mobile device may be an Internet-of-Things (IoT) device, a smartphone, a tablet computer, a notebook computer, a smart watch, and a smart band.

Having obtained the image, a representation of the at least a part of the surface is derived from the image, the representation comprising a set of values respectively representing a corresponding set of height levels of corresponding sections of the at least a part of the surface. In an exemplary embodiment, deriving the representation may be understood to correspond to or comprise converting or causing converting the image into a two-dimensional matrix, where each dimension of the matrix corresponds to a spatial dimension of the image (and/or sealed unit) and wherein each entry of the matrix represents a height of a corresponding section of the image. In such case, generating a string of characters based on the representation of the at least a part of the surface, the string of characters comprising at least a first portion representative of the set of height levels of the corresponding sections of the at least a part of the surface may in an exemplary embodiment be understood as appending entries of the matrix one after the other to generate the first portion of the string of characters.

In the following, a simplified example is explained disclosing a simplified way, according to which a representation of the at least a part of the surface (in this example a matrix representing perceived heights of the at least a part of the surface) is used for generating a string of characters. For example, an image may be converted into a square matrix of dimension n, i.e. an n×n matrix (the concept being similarly applicable to a non-square matrix). Thereby, each entry of the matrix represents a perceived height of a portion of the image corresponding to the entry, whereby each dimension of the matrix represents a corresponding dimension of the image (e.g. n×n may correspond to height×width of the image). In an exemplary embodiment, entries of the matrix are normalized, e.g. an entry representing a largest perceived height within the image is set to a value equal to 1 and an entry representing a smallest perceived height within the image is set to a value equal to 0. This advantageously helps to reduce or even eliminate an effect different lighting conditions may have on the heights perceived by a camera taking the image of the at least part of the surface.

The normalized height values included in the matrix are rounded (e.g. to two digits after a comma) and then represented in binary form. Thereby, different representations may be achieved by multiplying each value by a predefined rounding factor (e.g. by $1, 2, \ldots 2^k$) in accordance with the amount of rounding before converting the values into binary form. This parameter is suitable to adjust e.g. a length of resulting strings of characters and a degree of differentiation of different strings of characters.

The first portion of the string of characters can then be generated from the binarized matrix for example by appending the rows of the matrix one after the other to generate the string of characters (numbers).

It is noted that, if necessary or desired, the image may be subjected to processing such as filtering in order to remove imperfections resulting e.g. from imperfect optics, imperfect lighting, or the like. In other words, in an exemplary embodiment, deriving the representation from the image may comprise employing a filtering processing.

In an exemplary embodiment, the set of height levels of the corresponding sections of the at least a part of the surface corresponds to a set of height levels as perceived e.g. by the camera when obtaining the image under a given lighting condition. It is noted that a different lighting condition may thus result in a different set of height levels.

The second portion of the string of characters allows for quantifying differences in strings of characters e.g. as a result of different lighting conditions and/or as a result of differing surface structures. The second portion of the string of characters is generated based on a function of the representation and/or of the first portion of the string of characters, the function being in an exemplary embodiment a mathematical and/or statistical function of the representation and/or of the first portion of the string of characters. For example, the statistical function is in an exemplary embodiment a most-recurring function and/or an averaging function. For example, in a simplified case, a 4×4 matrix representation can be converted into a 2×2 matrix representation by applying e.g. one of such statistical functions to each one of 4 2×2 segments of the 4×4 matrix. Generating the second portion based on the 2×2 matrix allows applying a metric function in a reduced search space. As opposed for example to a hash value and/or a checksum, the statistical function is chosen to be less sensitive to small changes in the first portion of the string of characters and/or the representation. In this way, for example, small variations in lighting conditions when obtaining the image of the at least part of the surface, which may result in small changes in the representation (individual perceived height values) and/or the first portion of the sequence of characters may then result in correspondingly small changes in the second portion of the string of characters. In this way, the second portion of the string of characters is suited to provide a measure for a distance between different strings of characters. For example, a weighted average of values included in the first portion of the string of characters taking into account only values between 80% and 20% of a maximum value of the values of the first portion of the string of characters turned out to be a suitable function for generating the second portion.

Having generated the string of characters, information (e.g. data) representing the string of characters is associated with identification information of the sealed unit. In an exemplary embodiment, associating the information representing the string of characters with the identification information of the sealed unit comprises storing or causing storing the information representing the string of characters with the identification information of the sealed unit. For example, in case the at least one first apparatus corresponds to or is comprised by the mentioned device, this device may comprise or may be connected to a dedicated database for storing the identification information in association with the string of characters. Similarly, in case of the at least one first apparatus being a mobile device, the identification information may be stored in association with the string of characters in a corresponding storage of the mobile device.

In an alternative or additional exemplary embodiment, associating the information representing the string of characters with the identification information of the sealed unit comprises providing the information representing the string of characters in association with the identification information of the sealed unit to be accessible by at least one external network device, in particular via a communication path. Thereby, in an exemplary embodiment, the at least one external network device corresponds to or is comprised by a network server and/or server cloud. Thus, for example, the device and/or the mobile device may transmit the information representing the string of characters together with the identification information to a server and/or server cloud to be stored at the server and/or the server cloud.

In the context of the present disclosure, "communication path" is to be understood as a (bi-directional) wireless and/or wired network connection i.e. a wireless connection that enables a network entity to transmit and receive data via said connection. Examples of a wireless connection include a wireless communication path or link in a wireless communication network, in particular a terrestrial wireless communication network like a Wireless Local Area Network (WLAN) or a cellular network. WLAN is for example specified by the standards of the IEEE 802.11 family (http://www.ieee.org/). A cellular network may for example be a mobile phone network like a 2G/3G/4G/5G cellular communication network. The 2G/3G/4G/5G cellular radio communication standards are developed by the 3GPP and presently available under http://www.3gpp.org/. A wireless connection may further include a Device-to-Device (D2D) communication path. Examples of a wired connection include a Local Area Network (LAN) connection, and/or any further wired computer connection, e.g. a bus, in particular a Universal Serial Bus (USB), connection, and/or in particular an internet connection.

As mentioned, with the string of characters being associated with the identification information, in particular with the string of characters being stored in a database, it becomes possible to verify validity of a sealed unit and/or to verify intactness of the seal. For example, a device for verifying validity of the sealed package and/or intactness of the seal may as an example of the at least one second apparatus, be installed at a pharmacy, at a medical doctor's office, at a hospital and/or a different medical facility, and/or may correspond to a smartphone of a medical doctor, of a healthcare worker and/or of a patient. The device may be configured for obtaining a string of characters e.g. from an image of a surface of the sealed unit under inspection, in particular employing the steps of obtaining, deriving and generating described in the context of the method according to the first aspect. It is then possible to check if information representing the string of characters is present in a database.

Accordingly, a method according to the second aspect includes obtaining or causing obtaining first information representing a first string of characters with a first portion representative of a set of height levels of corresponding sections of at least a part of a surface of a first sealed unit. Thereby, in an exemplary embodiment, obtaining the first information comprises obtaining an image of at least a part of a surface of the sealed unit. In particular, in an exemplary embodiment, obtaining the first information comprises obtaining an image of at least a part of a surface of the first sealed unit corresponding to or comprising at least in part at least one of a bare surface portion of the sealed unit; at least a part of a label of the sealed unit; and/or at least a part of a seal for sealing the sealed unit. In other words, in an exemplary embodiment, obtaining or causing obtaining the image comprises obtaining or causing obtaining the image of at least a part of a bare surface portion of the sealed unit; of at least a part of a label of the sealed unit; and/or of at least a part of a seal for sealing the sealed unit.

As in case of the method according to the first aspect, the at least one second apparatus may comprise or correspond to a device connected to and/or comprising a digital camera or digital scanner and may thus be configured to obtain the image (e.g. a digital image) using the digital camera and/or the scanner.

Further, as in the case of the method according to the first aspect, in an exemplary embodiment, obtaining the first information comprises deriving or causing deriving a representation as discussed in case of the first aspect, the representation being a representation of the at least a part of the surface from the image, the representation comprising a set of values respectively representing a corresponding set of height levels of corresponding sections of the at least a part of the surface. Further, in an exemplary embodiment, obtaining the first information comprises generating the first string of characters based on the representation of the at least a part of the surface. In an exemplary embodiment, the first string of characters comprises a second portion, and the second portion of the first string of characters is generated based on the function of the representation and/or of the first portion of the first string of characters as discussed in case of the method according to the first aspect.

Alternatively or in addition, in an exemplary embodiment, obtaining the first information comprises receiving or causing receiving the first information via a network connection. Thereby, in an exemplary embodiment, the network connection comprises or corresponds to a communication path as disclosed above. Thus, in this embodiment, the at last one second apparatus may be comprised by or correspond to a network server and/or server cloud configured for carrying out processes of the method according to the second aspect.

In an exemplary embodiment, determining or causing determining, based on the obtained first information, whether or not the first string of characters is present in a database comprises comparing the first string of characters to at least one string of characters present in the database and determining whether or not the at least one string of characters present in the data base is equal to the first string of characters.

In an exemplary embodiment, determining, based on the obtained first information, whether or not the first string of characters is present in a database comprises determining or causing determining, based on the obtained first information, whether or not the first string of characters is stored in the database in association with identification information of the first sealed unit. In a further exemplary embodiment, the database is comprised by the at least one second apparatus and/or is connected to the at least one second apparatus via a wired and/or wireless network connection, whereby in an exemplary embodiment, the network connection corresponds to or comprises the above disclosed communication path. In the latter case, the database may e.g. be storage accessible via a network, e.g. storage comprised by or connected to a network server and/or a network server cloud.

If the method according to the second aspect determines that the first string of characters (and/or information thereof) is present in a database, the method according to the second aspect comprises outputting or causing outputting confirmation information.

In an exemplary embodiment, outputting the confirmation information corresponds to or comprises outputting a control signal configured for causing an external apparatus (in an exemplary embodiment an apparatus directly or indirectly connected to the at least one second apparatus, e.g. via the disclosed communication path) to perform a predetermined operation. For example, in an exemplary embodiment, the external apparatus corresponds to a conveyor belt and the predetermined operation corresponds to or comprises causing the conveyor belt to start or continue transport of the sealed unit. Such conveyor belt may be placed in a facility for distribution and/or control of pharmaceutical products or medical tools and may be part of a distribution, control or sorting machine. It is noted that the sealed unit may correspond more generally to a sealed consignment unit. For example in such case, in an exemplary embodiment, the at least one second apparatus configured for employing a method according to the second aspect may correspond to a control portion of a sorting machine placed in a facility of a logistics provider and the control signal may similarly cause a conveyor belt connected to or comprised by the sorting machine to start or continue transport of the sealed consignment unit. In case the sealed unit corresponds to a sealed consignment unit, in an exemplary embodiment, the identification information corresponds to or comprises identification information of an origin of the sealed consignment unit, a destination address of the sealed consignment unit, identification information of goods carried by the consignment unit, a serial number of an item carried by the consignment unit and/or a parameter characteristic of a physical property (e.g. weight, size and/or volume) of one or more items carried by the consignment unit.

In an alternative or additional exemplary embodiment, outputting the confirmation information corresponds to or comprises outputting or causing outputting information verifying the first sealed unit, in particular via a display comprised by the at least one second apparatus. For example, the at least one second apparatus may comprise or may be connected to a display for displaying the information verifying the first sealed unit to a user of the at least one second apparatus, e.g. to a patient, a medical doctor and/or to personnel of a doctor's office, of a pharmacy and/or of a hospital. For example, in such case, the display may show a message such as "confirmed", "medicine X confirmed" or the like.

Further, alternatively or in addition, in an exemplary embodiment outputting the confirmation information corresponds to or comprises outputting or causing outputting identification information of the sealed unit associated with the first string of characters in the database (e.g. stored in the database in association with the first string of characters).

For example, in case the sealed unit is sealed package including a certain type of medicine, and if the at least one second apparatus is comprised by and/or corresponds to a mobile device used by a patient, a display of the mobile device employing a method in accordance with such exemplary embodiment of the method according to the second aspect may output a name of the medicine (an example of identification information of the sealed unit) included in the sealed package which can be compared by the patient e.g. with a name of the medicine written on the sealed package for confirmation. If the name of the medicine derived from the database and outputted in this way matches the name of the medicine written on the sealed package, the patient may confirm that the sealed package is genuine and includes genuine medication with a high probability.

Thus, outputting the confirmation information corresponds to or comprises at least one of:
  outputting a control signal configured for causing an external apparatus to perform a predetermined operation;
  outputting or causing outputting, in particular via a display of the at least one second apparatus, confirmation information verifying the first sealed unit;
  outputting or causing outputting, in particular via a display of the at least one second apparatus, confirmation information corresponding to or comprising identification information of the sealed unit associated with the first string of characters in the database.

In an exemplary embodiment, if the first string of characters is not present in the database, the method comprises determining, based on a metric function, whether or not at least one second string of characters is present in the database, a distance of which to the first string of characters is below a first predefined threshold. In other words, if no exact match is present in the database, the method determines whether or not a string of characters (a code) is stored in the database that is similar to the string of characters of the sealed unit under inspection.

As mentioned above, the second portion of the string of characters is generated using a function that varies little if perceived height levels vary little accordingly. It may for example be assumed that lighting conditions are different when inspecting a sealed unit as compared to lighting conditions when a string of characters was initially associated with identification information of the sealed unit e.g. shortly after the sealed unit was generated. While such lighting conditions may result in variations in height levels perceived by corresponding cameras, the function for generating the second portion is chosen such that such variations in lighting conditions result in smooth (continuous), small variations of strings of characters generated from images taken under such differing lighting conditions. Applying the metric function to such strings of characters that correspond to a same sealed unit but are derived from images of the sealed unit taken under differing lighting conditions may thus result in a distance value that is below a suitably defined threshold.

It is noted that a metric function is in an exemplary embodiment defined such that two identical strings or respective portions thereof have a distance of zero and that a triangular inequality allows sorting of strings and/or indexing of strings based on the metric. In an exemplary embodiment, the metric function corresponds to or is based on a discrete metric, and may for example be based on counting a number of equal elements in respective matrices representing respective surface portions. In an alternative element, a metric is a Euclidian metric.

Further, if at least one second string of characters is present in the database, the distance of which to the first string of characters is below the first predefined threshold, the method according to the second aspect comprises outputting or causing outputting the confirmation information disclosed above.

Thus, in the exemplary embodiment, the method according to the second aspect advantageously allows not only searching the database for exact matches of a given string of characters for example implying that lighting conditions at a registering stage (e.g. when employing the method according to the first aspect) are the same also at a verifying stage (e.g. when employing the method according to the second aspect). To the contrary, by including the second portion into the string of characters, the method allows for verifying if a sealed unit has been registered in the database even when different lighting conditions have been present at the two stages. Thus, for example a patient and/or medical personnel may perform a verification of a sealed unit (employing the method according to the second aspect) essentially under arbitrary lighting conditions (e.g. at a patient's home and/or at a doctor's office) without having to simulate lighting conditions present when the sealed unit was initially registered.

In order to further enhance reliability of verifying a sealed unit, in an exemplary embodiment, if the first string of characters is not present in the database, i.e. if no exact match is found, the method according to the second aspect may generate variations (at least one variation) of the first string of characters representing the structure (e.g. the microstructure) of the at least a part of the surface of the first sealed unit as perceived under different lighting conditions (at least one different lighting condition). Thereby, a different lighting condition corresponds to a different set of (perceived) height levels.

To this end, the method according to the second aspect may in an exemplary embodiment generate (or cause generating) at least one first model string of characters (at least one modelled variation of the first string of characters) representative of a first model set of height levels of corresponding sections of the at least a part of the surface of the first sealed unit, e.g. by (e.g. mathematically) simulating the perceived height levels under a different lighting condition and the corresponding representation. Thus, in an exemplary embodiment, the method according to the second aspect further comprises a step (a) of obtaining or causing obtaining at least second information representing at least one first model string of characters with a first portion representative of a first model set of height levels of the corresponding sections of the at least a part of the surface of the first sealed unit. In an exemplary embodiment, the first model set of height levels corresponds to a set of height levels as perceived, e.g. by a camera, e.g. comprised by or connected to the at least one second apparatus, under a different lighting condition as in case of the set of height levels corresponding to the first portion of the first string of characters. Modeling the height levels under a corresponding different lighting condition, in an exemplary embodiment, the method according to the second aspect comprises for each one of the at least one first model string of characters, obtaining the first model set of height levels of the corresponding sections of the at least a part of the surface of the first sealed unit by calculating the height levels of the corresponding sections assuming different lighting conditions.

Having thus generated the variations (at least one variation) of the first string of characters representing the structure (e.g. the microstructure) of the at least a part of the surface of the first sealed unit as perceived under different lighting conditions (at least one different lighting condition), the method according to the second aspect may in this embodiment determine whether or not a string of characters is present in the database that is similar to any one or more of the generated variations of the first string of characters (and/or to the first string of characters). Thus, the method according to the second aspect comprises in an exemplary embodiment a step (b) of determining, based on a metric function, whether or not at least one second string of characters is present in the database, a distance of which to the at least one first model string of characters is below a second predefined threshold (which may correspond to the first predefined threshold). Here, the metric function may correspond to the metric function disclosed above. Then, in a case in which at least one second string of characters is present in the database, the distance of which to the at least one first string of characters and/or the first model string of characters is below the second predefined threshold, the method comprises a step (c) of outputting or causing outputting the confirmation information disclosed above.

In an exemplary embodiment, if at least one second string of characters is determined to be present in the database, the at least one second string of characters comprising a first portion representative of a set of height levels of corresponding sections of at least a part of a surface of at least one respective second sealed unit (potentially corresponding to the first sealed unit as perceived under different lighting conditions) corresponding to the at least one second string of characters and the distance of which to the first string of characters and/or to the at least one first model string of characters is below the first and/or the second predefined threshold, the method further comprises the following steps (a), (b) and (c). In other words, in case at least one second string is present in the database, that is associated with a corresponding (at least one) second sealed unit, whereby a distance (a similarity) of the at least one second string is below a predefined threshold value, in the exemplary embodiment, the method according to the second aspect performs the following steps (a), (b) and (c).

In a step (a), as in case of the first string of characters disclosed above, the method generates variations (at least one variation) representing the structure (e.g. the microstructure) of the at least a part of the surface of the at least one second sealed unit as perceived under further different lighting conditions (at least one different lighting condition). Again, a different lighting condition corresponds to a different set of (perceived) height levels. Thus, in the exemplary embodiment the step (a) is a step of obtaining or causing obtaining, for each one of the at least one second string of characters, at least third information representing at least one respective second model string of characters corresponding to the at least one second string of characters with a first portion being representative of a second model set of height levels of corresponding sections of at least a part of the surface of the respective second sealed unit corresponding to the at least one second string of characters. As in case of the first model string(s) of characters disclosed above, in an exemplary embodiment for each one of the at least one second model string of characters the second model set of height levels of the corresponding sections of the at least a part of the surface of the second sealed unit is obtained by calculating the height levels of the corresponding sections assuming different lighting conditions.

Then, the variations of the second string of characters and/or the second string of characters are compared to the variations of the first string of characters and/or the first string of characters in order to determine a pair of second string of characters or variation thereof and first string of characters or variation thereof for which a corresponding distance is smallest (and corresponding similarity is highest) and/or whether or not such pair exists in the database, a mutual distance of which is below a third predefined threshold (which may correspond to any one of the first or the second predefined threshold).

It is noted that in all cases discussed herein, a distance between a given string of characters (e.g. the first string of characters, the at least one first model string of characters, the second string of characters, and/or the at least one second model string of characters) and a different string of characters (e.g. a different one of the first string of characters, the at least one first model string of characters, the second string of characters, and/or the at least one second model string of characters) is in an exemplary embodiment determined based on a metric function (e.g. the metric function disclosed above) and based on a second portion comprised by the first string of characters, the at least one first model string of characters, the second string of characters, and/or the at least one second model string of characters.

In other words, in an exemplary embodiment, the first string of characters, the at least one second string of characters, the at least one first model string of characters and the at least one second model string of characters each comprise respective second portions; and wherein respective mutual distances between the first string of characters, the at least one second string of characters, the at least one first model string of characters and the at least one second model string of characters are determined based on the metric function and based on the respective second portions.

For example in this way, it may be determined whether or not such pair exists in the database, a mutual distance of which is below the third predefined threshold. In other words, in an exemplary embodiment, the step (b) is a step of determining or causing determining whether or not at least one string of characters of the at least one second string of characters and the at least one corresponding second model string of characters is present in the database for which a distance to any one of the first string of characters and the at least one first model string of characters is below a third predefined threshold.

Having determined whether or not such string is present in the database, the method may further proceed to outputting or causing outputting confirmation information as disclosed above. In particular, in an exemplary embodiment, the method may proceed to (c): outputting or causing outputting, confirmation information if at least one second string of characters is present in the database, the distance of which to the at least one first model string of characters is below the second predefined threshold.

In the alternative case, in an exemplary embodiment, the method comprises a step (d) of outputting or causing outputting, in particular via a display of the at least one second apparatus, corresponding information if no second string of characters is present in the database, the distance of which to the at least one first model string of characters is below the second predefined threshold. In an exemplary embodiment, the information output in this case is non-affirmative information (e.g. "sealed unit not accepted").

In order to further improve reliability of a registering method (e.g. of the method according to the first aspect) and of a verification method (e.g. of the method according to the second aspect), the string of characters, the first string of characters, the second string of characters, the at least one first model string of characters, and/or the second model string of characters further comprises in an exemplary embodiment a third portion different from the first and/or the second portion and being determined based on a hash function of the first portion and/or the second portion and/or comprising a checksum of the first portion and/or the second portion. For example, using a hash function, for example the first portion of the string of characters can be mapped to a corresponding hash code of predefined size. Alternatively or in addition, the third portion may comprise a checksum e.g. of the first portion of the string of characters which may advantageously employed to detect errors that may have occurred when handling any string of characters and/or to verify corresponding data integrity.

As mentioned above, in an exemplary embodiment of the first and/or the second aspect, obtaining the image comprises obtaining the image using a digital camera or a scanner. As further mentioned above, a set of height values may vary in accordance with lighting conditions employed during the registering stage and/or the verification stage. In this connection, it was found that precision and reliability of the methods according to the first and the second aspects may even further be enhanced by controlling the lighting conditions during the registering and/or during the verification stage. It was in particular found that use of a particular light source may have an advantageous effect, e.g. depending on the sealed unit. Thus, in an exemplary embodiment of the first and/or the second aspect, obtaining the image of the at least a part of the surface comprises applying or causing applying ultraviolet, UV, infrared, IR, and/or white light to the at least a part of the surface.

As disclosed above, the methods according to the first and the second aspect may be advantageously employed for registering (the method according to the first aspect) and for verifying (the method according to the second aspect) a sealed unit. A sealed unit addressable by methods according to the first and/or second aspect may in an exemplary embodiment correspond to a sealed package for a pharmaceutical product.

In an exemplary embodiment, identification information of the sealed unit corresponds to or comprises an origin of the pharmaceutical product, a batch number of the pharmaceutical product, a type of the pharmaceutical product, an identification number and/or code of the pharmaceutical product, a name of the pharmaceutical product, an expiration date of the pharmaceutical product, and/or information identifying an addressee of the pharmaceutical product, e.g. a name of the addressee, a place of birth of the addressee, date of birth of the addressee and/or residence of the addressee.

In an exemplary embodiment, identification information of the sealed unit is present on a surface of the sealed unit, e.g. in form of a serial number, e.g. a numerical and/or alphanumerical serial number, in written form, and/or in form of a one or two-dimensional bar code (e.g. a QR code) and/or in form of electromagnetic, electric or magnetic type information (to be read by sensors of a read-out device based on electromagnetic signals, electric or magnetic fields, e.g. RFID and/or NFC sensors).

It is to be understood that the presentation of the invention in this section is merely by way of examples and non-limiting.

Other features of the invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not drawn to scale and that they are merely intended to conceptually illustrate the structures and procedures described herein.

DETAILED DESCRIPTION OF EXAMPLE EMBODIMENTS OF THE INVENTION

Figure 1:
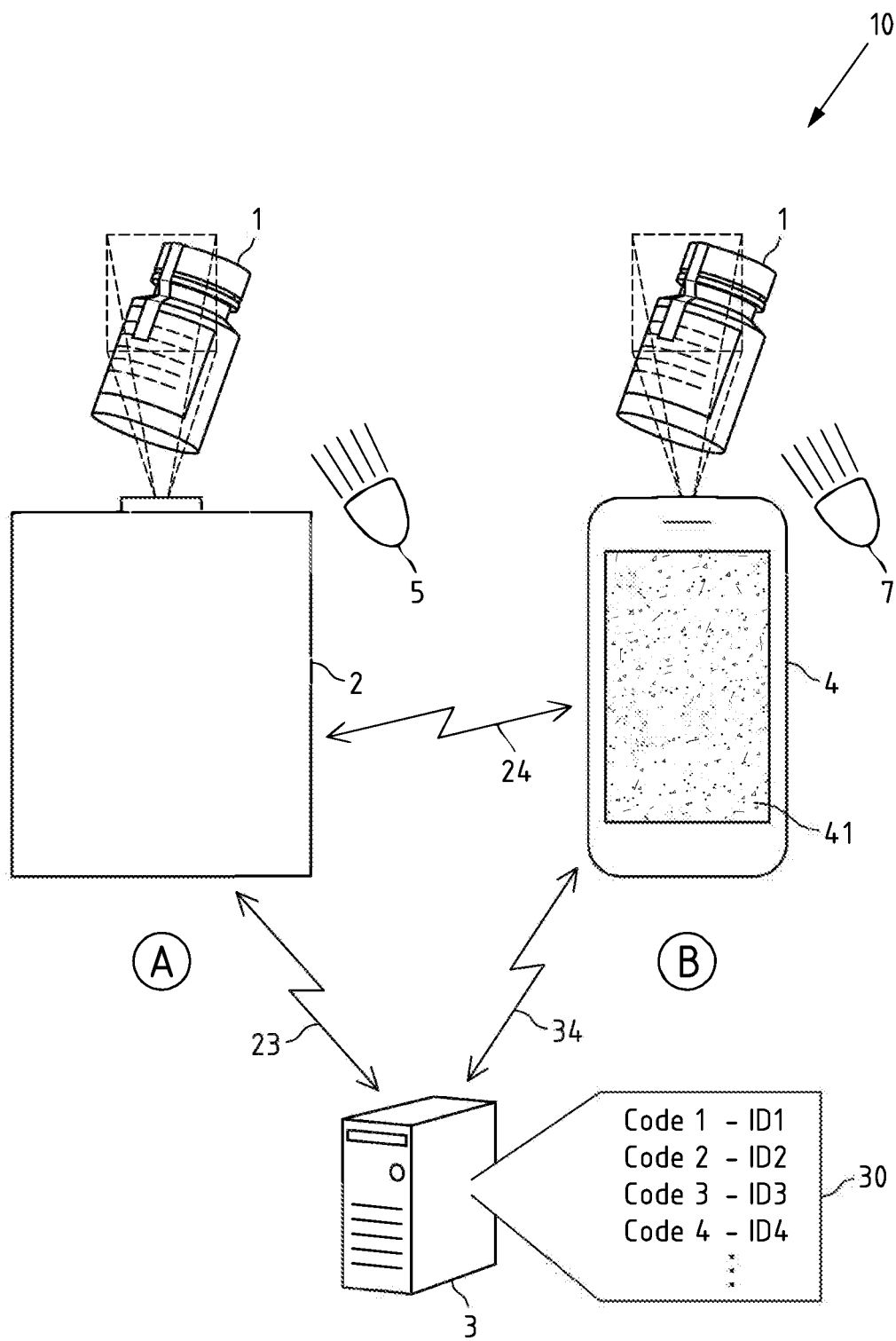
FIG. 1 is a block diagram of an exemplary embodiment of a system according to the invention.

FIG. 1 is a schematic illustration of an example embodiment of a system 10 comprising a registration device 2 (an example of the at least one first apparatus), a mobile device 4 (an example of the at least one second apparatus) and a server 3 storing database 30. It is noted that registration device 2 may incorporate and/or correspond to a further mobile device. Further, each of registration device 2 and mobile device 4 comprises or is connected to a camera (not shown) for acquiring an image of drug package 1 (an example of a sealed unit addressable by a method according to the first and by a method according to the second aspect) shown in FIG. 1. It is further noted that instead of or in addition to at server 3 and mobile device 4, the respective steps of a method in accordance with the second aspect may be similarly performed by a single dedicated device comprising a corresponding database (or being connected to a corresponding network database).

Drug package 1 including a pharmaceutical product such as pharmaceutical pills is shown at stage A of FIG. 1 being under registration and at stage B of FIG. 1 being verified. In other words, registration stage A may correspond to a stage after production of the drug package 1 at which drug package 1 is registered in combination e.g. with details of its content (e.g. in combination with identification information of the pharmaceutical product such as the product's name, details about its ingredients, the product's origin, a serial number of the product, etc.).

In FIG. 1, verification stage B corresponds to a later stage at which drug package 1 is verified, i.e. at which it is checked if drug package 1 is a counterfeit package. Such later stage may for example correspond to a situation where a patient verifies a drug package, e.g. mobile device 4 being the patient's mobile device, a situation where a healthcare worker in a hospital or different medical facility verifies a drug package, e.g. mobile device 4 being the healthcare worker's mobile device, etc. While the figures are focused on an application to medical packages, it is noted that in addition or alternatively, aspects of the present disclosure are likewise applicable e.g. to general logistics situations, where a sealed consignment unit takes the role of drug package 1, being inspected for validity e.g. at a logistics facility by a worker of a logistics company, mobile device 4 in this situation being a mobile device of the worker, or being replaced e.g. by a sorting machine configured for performing a method according to the second aspect. Light sources 5 and 7 (which may comprise one or more light sources) provide a respective lighting conditions for the registration process and may correspond to or comprise respective ultraviolet (UV), infrared (IR) and/or white light sources.

As shown in FIG. 1, registration device 2 acquires (an example of obtaining) an image of at least part of a surface of drug package 1. Based on the obtained image, registration device 2 then derives a representation of the at least a part of the surface from the image, e.g. a two-dimensional matrix comprising a set of values respectively representing a corresponding set of height levels of corresponding sections of the at least a part of the surface. Based on the representation, registration device 2 then generates a string of characters (a code) comprising a first portion representative of the set of height levels and a second portion generated based on a function (a mathematical function) of the first portion. In an exemplary embodiment, the code further comprises a third portion which corresponds to or comprises in particular a checksum of the first portion. The registration device 2 then associates information (e.g. data) representing the string of characters with identification information of the sealed unit. To this end, registration device 2 for example transmits the information representing the string of characters in association with identification information such as a name of the drug contained by the drug package and/or a serial number to server 3 via communication path 23. Alternatively or in addition, in a case in which a corresponding database is stored at registration device 2, registration device 2 may store the information representing the string of characters in association with the identification information of the sealed unit at the database of the registration device 2.

As further shown in FIG. 1, at stage B, mobile device 4 performs actions for verification of the drug package 1. For example, mobile device 4 obtains an image of at least a part of a surface of drug package 1 using e.g. a digital camera comprised by mobile device 4. Based on the obtained image, mobile device 4 then derives a representation of the at least a part of the surface from the image, for example a two-dimensional matrix comprising a set of values respectively representing a corresponding set of height levels of corresponding sections of the at least a part of the surface. It is noted that parameters such as matrix dimension may be preset and may be employed commonly at registration device 2 and at mobile device 4. Based thereon, mobile device 4 then generates a first string of characters based on the representation of the at least a part of the surface. In this way, mobile device 4 thus obtains first information representing the first string of characters. It is noted that alternatively, mobile device 4 receives the first information via a network connection, for example in a case in which verification processing is outsourced to a network device, e.g. to server 3 which may for example process an image obtained at mobile device 4 and which may sent the first information to device 4 via communication path 34. Based on the obtained first information, mobile device 4 may then determine whether or not the first string of characters is present in a database.

Thereby, the database may be a database comprised by or connected to mobile device 4 (having obtained the corresponding information from registration device 2 via communication path 24). Alternatively, as shown in FIG. 1, mobile device 4 may determine, based on the obtained first information, whether or not the first string of characters is present in database 30 via communication with server 3 (an example of an external network device) connected to database 30 via communication path 34. In the affirmative case, mobile device 4 may e.g. output confirmation information by displaying a confirmation message (e.g. "drug package verified") using display 41 of mobile device 4. Alternatively, or in addition, mobile device 4 may output confirmation information by displaying identification information of sealed unit 1 associated in database 30 with the first string of characters using display 41. If the first string of characters is not present in the database, mobile device 4 may determine based on the metric function disclosed above, whether or not at least one second string of characters is present in the database, a distance of which to the first string of characters and/or to the at least one first model string of characters disclosed above is below a first predefined threshold. If at least one second string of characters is present in the database, the distance of which to the first string of characters and/or the first model string of characters is below the first predefined threshold, mobile device 4 may output said confirmation information, e.g. via display 41.

It is noted that any of communication paths 23, 24 and 34 described above may be a direct or indirect communication path. For example, any of communication paths 23, 24 and 34 may comprise one or more hops, for example one or more communication links or communication connections. In the context of the present disclosure communication paths are to be understood as (bi-directional) wireless communication connections like 2G/3G/4G/5G cellular wireless connections, Device-to-Device (D2D) communication paths, (bi-directional) wireless communication connections such as Wireless Local Area Network (WLAN) connections, and/or wired computer connections such as buses including in particular USB connections.

Figure 2:
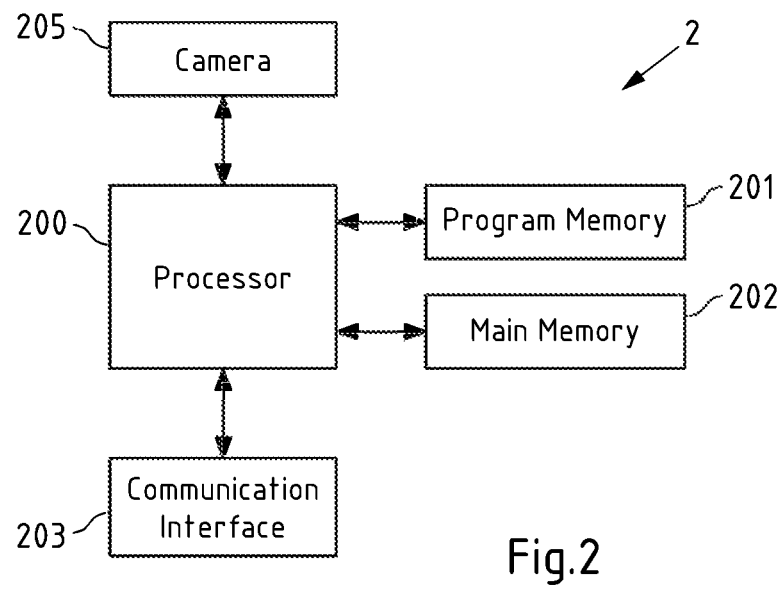
FIG. 2 is a block diagram of an exemplary embodiment of an apparatus according to the first aspect of the invention.

FIG. 2 is a block diagram of an exemplary embodiment of registration device 2 (an example of the at least one first apparatus). In the following, it is assumed that registration device 2 of system 10 of FIG. 1 corresponds to registration device 2 of FIG. 2.

Registration device 2 comprises a processor 200. Processor 200 may represent a single processor or two or more processors, which are for instance at least partially coupled, for instance via a bus. Processor 200 executes a computer program code to perform any one embodiment of the disclosed method according to the first aspect (e.g. the steps of any one embodiment of the disclosed method) stored in program memory 201 or a part thereof (e.g. at least some steps of any one embodiment of the disclosed method), and interfaces with a main memory 202. Accordingly, program memory 201 may contain an operating system for processor 200. Some or all of memories 201 and 202 may also be included into processor 200. One of or both of memories 201 and 202 may be fixedly connected to processor 200 or at least partially removable from processor 200, for example in the form of a memory card or stick.

Processor 200 further controls a communication interface 203 which is configured to communicate via a communication network. Registration device 2 may use communication interface 203 to communicate with external network devices such as server 3 (via communication path 23) or mobile device 4 (via communication path 24). In the following, it is assumed that communication interface 203 is a wireless or wired communication interface configured for communicating using (bi-directional) communication connections like 2G/3G/4G/5G cellular wireless connections, Device-to-Device (D2D) communication paths, (bi-directional) wireless communication connections such as Wireless Local Area Network (WLAN) connections, or wired computer connections such as buses including in particular USB connections. In an exemplary embodiment, communication interface 203 may be or may comprise a 2G/3G/4G/5G and/or WiFi radio transceiver. For example, registration device 2 may use communication interface 203 to transmit information representing the string of characters associated with identification information of the sealed unit to server 3 via communication path 23 and/or to mobile device 4 via communication path 24.

Moreover, processor 200 controls a camera 205 (e.g. a digital camera) which is configured for obtaining a digital image of at least a part of a surface of drug package 1 (as shown in FIG. 1).

The components 201 to 205 of registration device 2 may for example be connected with processor 200 by means of one or more serial and/or parallel busses.

It is to be understood that registration device 2 may comprise various other components like a user interface for receiving user input.

Figure 3:
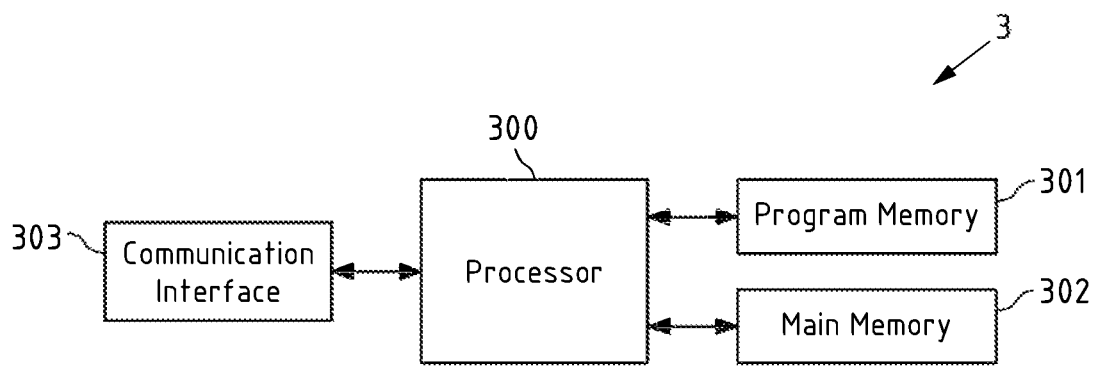
FIG. 3 is a block diagram of an exemplary embodiment of an apparatus according to the second aspect of the invention.

FIG. 3 is a block diagram of an exemplary embodiment of server 3 (which may be a further example of the at least one first and/or second apparatus). In the following, it is assumed that server 3 of system 10 of FIG. 1 corresponds to server 3 of FIG. 3. Server 3 is an example of the disclosed network device and may correspond to or comprise a network server and/or server cloud connected to a network such as a local area network and/or the Internet.

Server 3 comprises a processor 300. Processor 300 may represent a single processor or two or more processors, which are for instance at least partially coupled, for instance via a bus. Processor 300 executes a computer program code (e.g. computer program code causing server 3 to store information representing a string of characters in association with identification information of a sealed unit e.g. received from registration device 2, and/or to obtain first information representing a first string of characters with a first portion representative of a set of height levels of corresponding sections of at least a part of a surface of a first sealed unit, e.g. based on an image received from mobile device 4) stored in program memory 301, and interfaces with a main memory 302. Accordingly, program memory 301 may contain an operating system for processor 300. Some or all of memories 301 and 302 may also be included into processor 300. One of or both of memories 301 and 302 may be fixedly connected to processor 300 or may be at least partially removable from processor 300, for example in the form of a memory card or stick.

Processor 300 further controls a communication interface 303 which is configured for communicating via a communication network. Server 3 may use communication interface 303 to communicate with registration device 2 and/or with mobile device 4 of system 10 via said local area network and/or the Internet. Communication paths 23 and 34 may thus at least in part correspond to or comprise communication connections within such local area network and/or the Internet. Communication interface 303 may in addition or alternatively correspond to or comprise a wireless communication interface configured for communicating via a cellular network (e.g. to transmit and receive cellular radio signals). For example, communication interface 303 may be or may comprise a 2G/3G/4G/5G radio transceiver. It is however to be understood that the invention is not limited to this. Interface 303 may similarly be a wireless communication interface configured for communicating via a Device-to-Device (D2D) communication path or a (bi-directional) wireless communication connection in a Wireless Local Area Network (WLAN). For example, server 3 may use communication interface 303 to receive information representing a string of characters in association with corresponding identification information of a sealed unit from registration device 2 via communication path 23 and/or to transmit stored information to mobile device 4 via communication path 34.

The components 301 to 303 of server 3 may for example be connected with processor 300 by means of one or more serial and/or parallel busses.

It is to be understood that server 3 may comprise various other components like a user interface for receiving user input.

Figure 4:
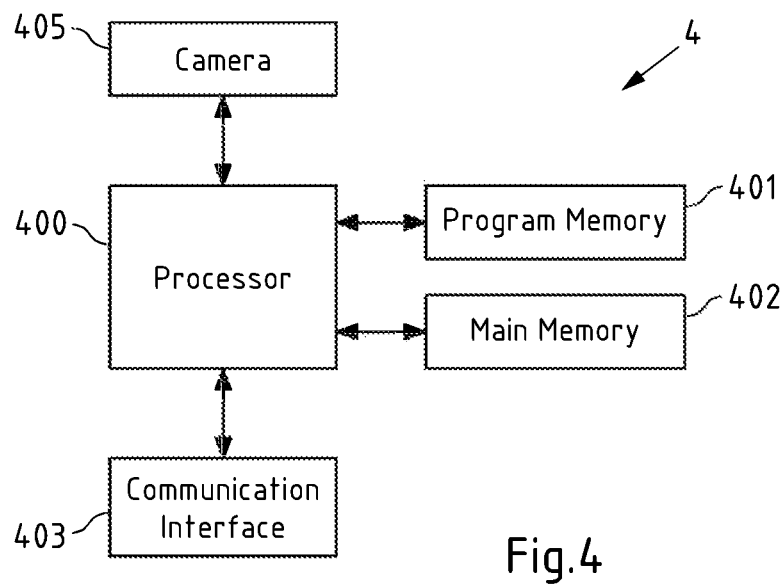
FIG. 4 is a block diagram of a further exemplary embodiment of an apparatus according to the second aspect of the invention.

FIG. 4 is a block diagram of an exemplary embodiment of mobile device 4 (a further example of the at least one second apparatus). In the following, it is assumed that mobile device 4 of FIG. 1 corresponds to mobile device 4 of FIG. 4. Mobile device 4 may thus correspond to a mobile device 4 used by a patient for verifying that a drug package is not a counterfeit drug package and that medicine included therein is thus trustable.

Mobile device 4 comprises a processor 400. Processor 400 may represent a single processor or two or more processors, which are for instance at least partially coupled, for instance via a bus. Processor 400 executes a computer program code stored in program memory 401 (e.g. computer program code causing mobile device 4 to perform any one embodiment of the disclosed method according to the second aspect (e.g. the steps of any one embodiment of the disclosed method) or a part thereof (e.g. at least some steps of any one embodiment of the disclosed method), when executed on processor 400), and interfaces with a main memory 402. Program memory 401 may also contain an operating system for processor 400 and further data. Some or all of memories 401 and 402 may also be included in processor 400. One of or both of memories 401 and 402 may be fixedly connected to processor 400 or at least partially removable from processor 400, for example in the form of a memory card or stick.

A program memory (e.g. program memory 201 and/or program memory 401) may for example be a non-volatile memory. The program memory (e.g. program memory 201 and/or program memory 401) may for instance be a FLASH memory (or a part thereof), any of a ROM, PROM, EPROM, MRAM or a FeRAM (or a part thereof) or a hard disc (or a part thereof), to name but a few examples. For example, a program memory may for instance comprise a first memory section that is fixedly installed, and a second memory section that is removable, for instance in the form of a removable SD memory card.

A main memory (e.g. main memory 201 and/or main memory 401) may for example be a volatile memory. It may for example be a DRAM memory, to give non-limiting example. It may for instance be used as a working memory for a processor (e.g. processor 200 and/or processor 400) when executing an operating system and/or programs.

Processor 400 further controls a communication interface 403 which is configured to communicate via a communication network. Mobile device 4 may use communication interface 403 to communicate with external network devices such as server 3 (via communication path 34) or registration device 2 (via communication path 24). In the following, it is assumed that communication interface 403 is a wireless or wired communication interface configured for communicating using (bi-directional) communication connections like 2G/3G/4G/5G cellular wireless connections, Device-to-Device (D2D) communication paths, (bi-directional) wireless communication connections such as Wireless Local Area Network (WLAN) connections, or wired computer connections such as buses including in particular USB connections. In an exemplary embodiment, communication interface 403 may be or may comprise a 2G/3G/4G/5G and/or WiFi radio transceiver. For example, mobile device 4 may use communication interface 403 to determine, based on the obtained first information, whether or not the first string of characters is present in database 30 via communication with server 3 via communication path 34.

Moreover, processor 400 controls a camera 405 (e.g. a digital camera) configured for obtaining a digital image of at least a part of a surface of drug package 1 (as shown in FIG. 1).

The components 401 to 405 of mobile device may for instance be connected with processor 400 by means of one or more serial and/or parallel busses.

It is to be understood that mobile device 4 may comprise various other components like a user interface for receiving user input.

Figure 5:
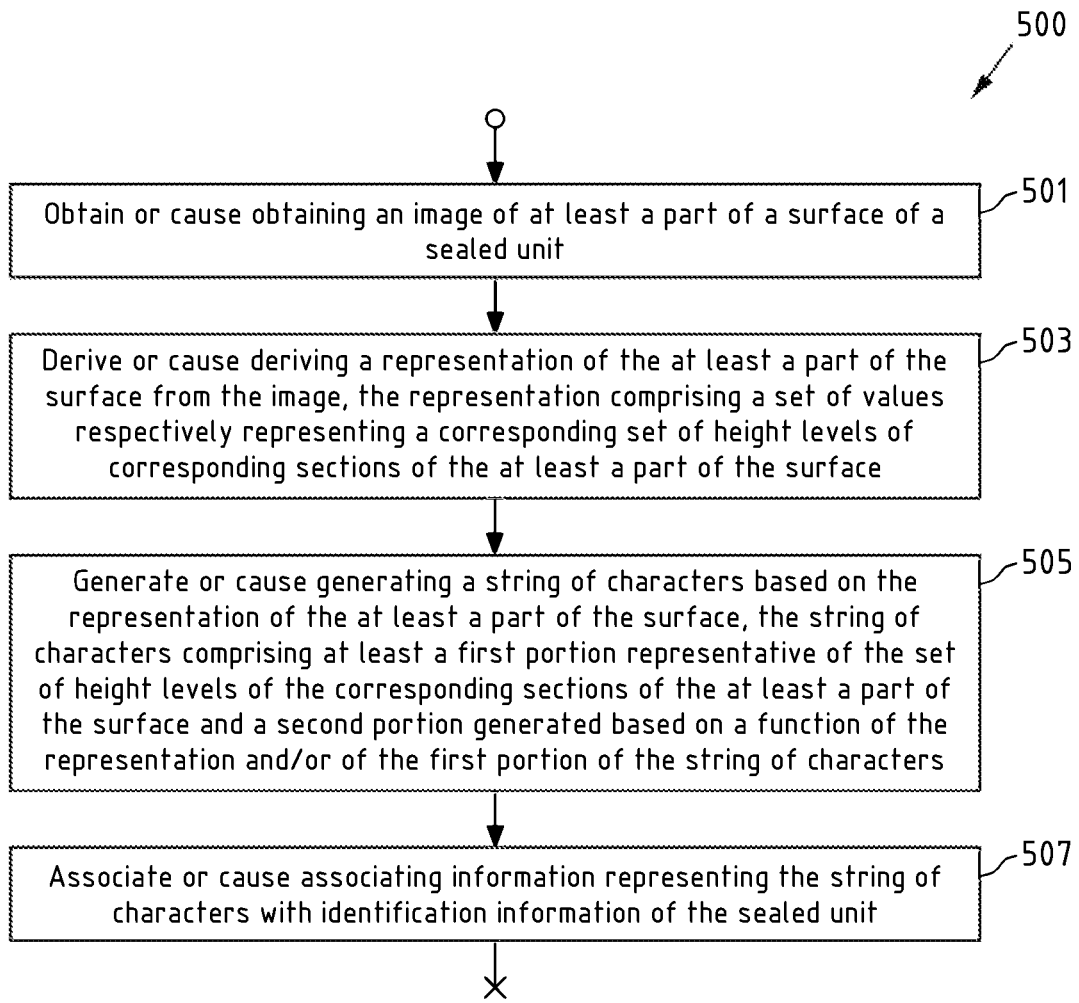
FIG. 5 is a flow chart illustrating an exemplary embodiment of a method according to the first aspect of the invention.

FIG. 5 is a flow chart 500 illustrating an exemplary embodiment of a method according to the first aspect of the invention. Without limiting the scope of the invention, it is assumed in the following that registration device 2 as disclosed above with respect to FIGS. 1 and 2 performs the steps of flow chart 500. It is noted that the steps of flow chart 500 could likewise be performed by a mobile device substituting or used in combination with registration device 2. In addition, it is further noted that the steps of flow chart 500 could likewise be performed at server 3, e.g. when obtaining an image taken at registration device 2 via network connection 23.

In a step 501, registration device 2 obtains an image of at least a part of a surface of a sealed unit, for example, registration device 2 obtains an image of at least a part of a surface of drug package 1 at registration stage A of FIG. 1, using camera 205.

In a step 503, registration device 2 derives a representation of the at least a part of the surface from the image, the representation comprising a set of values respectively representing a corresponding set of height levels of corresponding sections of the at least a part of the surface. For example, registration device 2 may perform processes of filtering the image for example for reducing artifacts due to imperfect optics and/or lighting conditions and may thereby optimize the image. Registration device 2 may then convert the image into a two dimensional matrix where each dimension represents a corresponding dimension of the image and where each entry represents a corresponding height value of a respective section of the image.

In a step 505, registration device 2 generates a string of characters based on the representation of the at least a part of the surface, the string of characters comprising at least a first portion representative of the set of height levels of the corresponding sections of the at least a part of the surface and a second portion generated based on a function of the representation and/or of the first portion of the string of characters. In a simple example, registration device 2 may place the entries of the matrix one after the other in order to obtain the first portion of the string of characters. Based thereon, using a statistical function such as a suitable averaging function, registration device 2 may generate the second portion of the string of characters as a portion which varies little when entries of the matrix vary little, e.g. as a result of small changes in lighting conditions. As explained above, the string of characters may further comprise a third portion comprising a checksum of the first portion for verifying the string of characters.

In a step 507, registration device 2 associates information representing the string of characters with identification information of the sealed unit. For example, registration device 2 may transmit information representing the string of characters in association with a name of a certain medicine included in the drug package and/or personal information of a patient for which the drug package is intended (e.g. an addressee of the drug package) to server 3 via communication path 23 to be stored in database 30.

Figure 6:
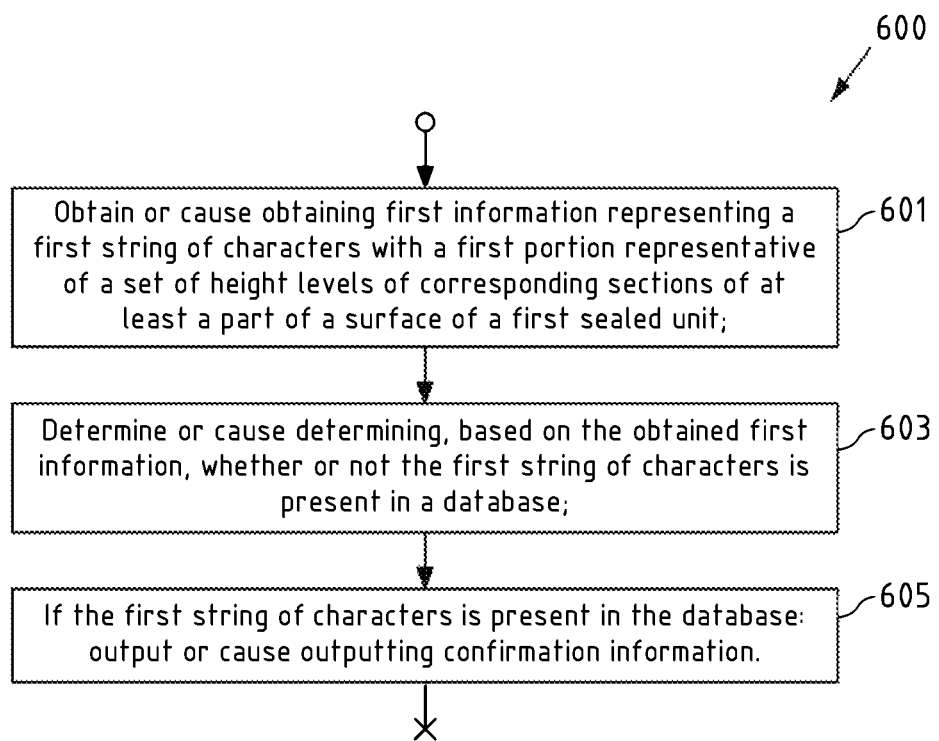
FIG. 6 is a flow chart illustrating an exemplary embodiment of a method according to the second aspect of the invention.

FIG. 6 is a flow chart 600 illustrating an exemplary embodiment of a method according to the second aspect of the invention. Without limiting the scope of the invention, it is assumed in the following that mobile device 4 as disclosed above with respect to FIGS. 1 and 4 performs the steps of flow chart 600. It is noted that the steps of flowchart 600 may further be performed by server 3 of FIG. 1. Further, in alternative embodiments, the steps of flowchart 600 may likewise be performed by one or more fixedly installed devices, installed e.g. at a medical facility and/or at a facility of a logistics provider where a corresponding verification process is carried out e.g. to detect and sort out counterfeit drug packages.

In a step 601, mobile device 4 obtains first information representing a first string of characters with a first portion representative of a set of height levels of corresponding sections of at least a part of a surface of a first sealed unit. As mentioned above, mobile device 4 may obtain an image of a part of a surface of drug package 1 at verification stage B of FIG. 1 using camera 405, may derive a representation of the surface from the image and may generate the first string of characters based on the representation. Further, for example, server 3 may perform step 601 by obtaining the first information from mobile device 4 via communication path 34.

In a step 603, mobile device 4 determines, based on the obtained first information, whether or not the first string of characters is present in a database. For example, mobile device 4 may determine whether or not the first string of characters is present in database 30 via communication with server 3 via communication path 34. Alternatively or in addition, server 3 may perform step 603 by determining whether or not the first string of characters is present in database 30.

In a step 605, if the first string of characters is present in the database, mobile device 4 outputs confirmation information. For example, mobile device 4 may display such confirmation information via display 41, e.g. mobile device may display a confirmation message such as "confirmed". Alternatively, server 3 may perform step 605 by causing mobile device 4 to display such confirmation message, by sending a corresponding message to mobile device 4 via communication path 34.

Figure 7A:
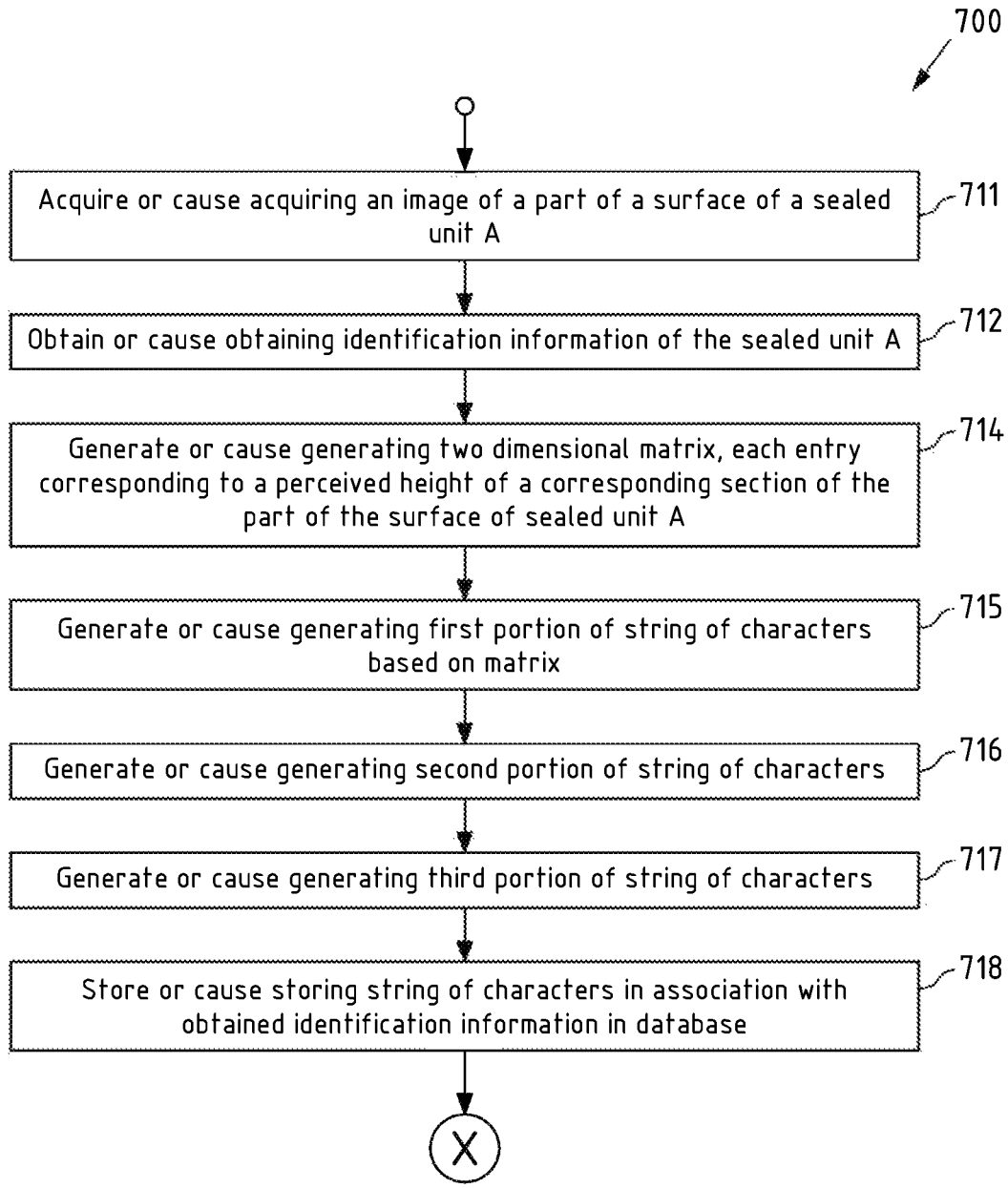
FIG. 7A is a first part of a flow chart illustrating a further exemplary embodiment of a method according to the invention.
Figure 7B:
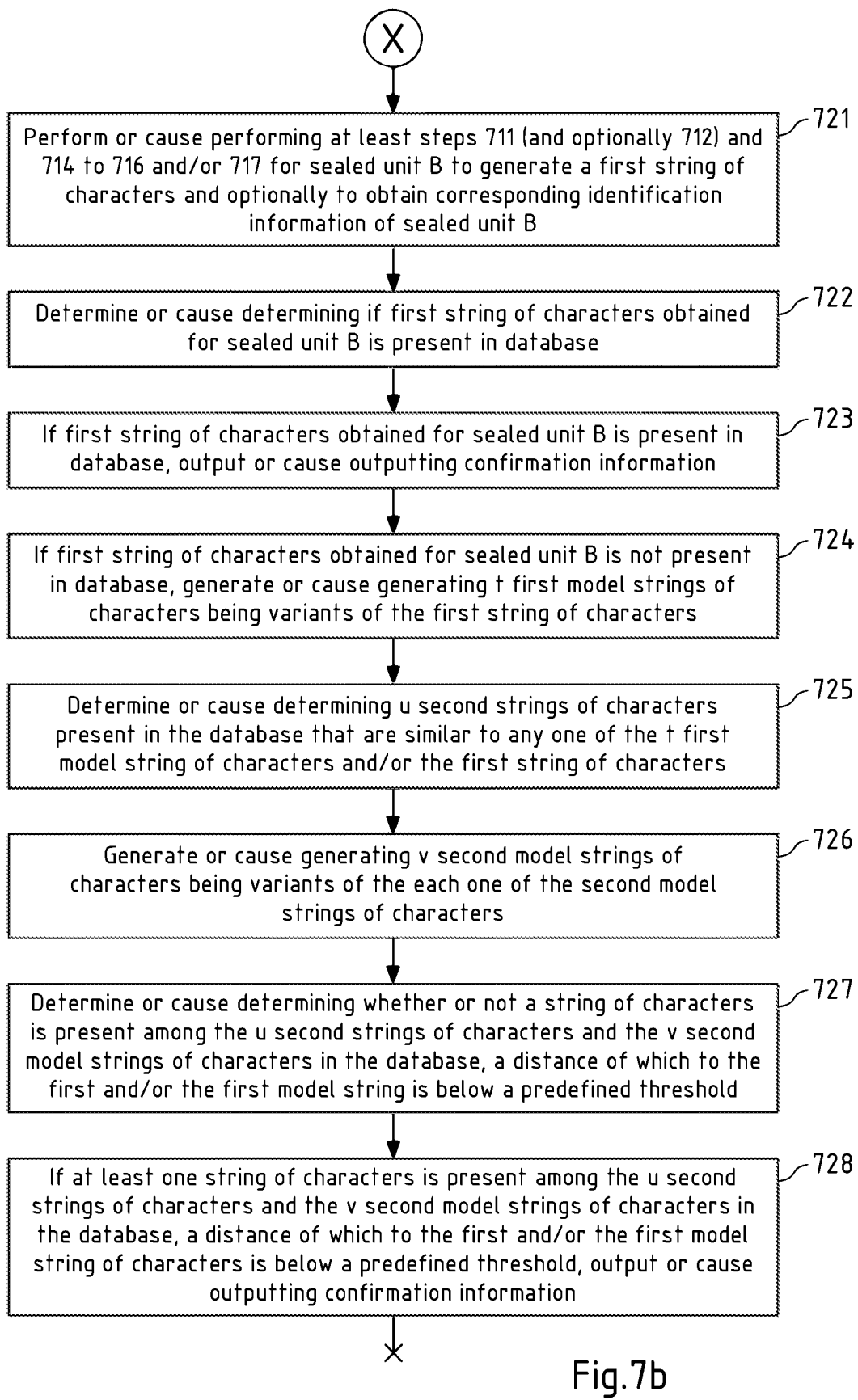
FIG. 7B is a second part of the flow chart of FIG. 7A.

FIG. 7A is a first part of a flow chart illustrating a further exemplary method 700 according to an exemplary embodiment of the invention and FIG. 7B illustrates the second part of method 700.

Without limiting the scope of the invention, it is assumed in the following that steps 711 to 718 of method 700 are exemplary steps of a registration process that may be carried out by registration device 2 as an example of an apparatus according to the first aspect. Further, steps 721 to 727 are steps of a verification process that may be performed by mobile device 4 as an example of an apparatus according to the second aspect in communication with server 3. It is noted, however, that steps 721 to 727 may be performed e.g. by a dedicated verification device (e.g. installed at a medical facility and/or at a facility of a logistics provider) with its own database or in communication with a database such as a network based database. In addition, it is noted that steps 711 to 718 and/or steps 721 to 727 may be performed by server 3.

Turning to FIG. 7A, in step 711, registration device 2 acquires an image of a part of a surface of a drug package A, i.e. a drug package to be registered (an example of a "first sealed unit" as referred to herein). In a step 712 (which may be performed before, after or simultaneously with step 711), registration device 2 obtains identification information of drug package A, e.g. by automatically reading text and/or image information from drug package A and/or via user input. As disclosed further herein, identification information may correspond to a serial number of drug package A, to a name and/or type of a medicine included in drug package A, and/or to personal information of a patient to which the drug package A is addressed.

Based on the obtained image, the registration device 2 generates in step 714 a two dimensional matrix, each entry of the matrix corresponding a perceived height of a corresponding section of the part of the surface of drug package A.

It is noted that the method may be further improved in terms of robustness if steps 711 to 714 are applied to more than one part of a surface of the drug package. For example, the steps 711 to 714 may be applied to different parts of the surface, the position of which is identifiable for corresponding steps applied in a later verification process such as surfaces with a predefined extension with respect to two or more edges of the drug package. In addition or alternatively, for each or at least one of such two or more parts of the surface to which steps 711 to 714 are applied, for example different resolutions and/or different sizes of the two dimensional matrix may be applied to introduce further redundancy.

In steps 715 to 717, registration device 2 generates a first, a second and (optionally) a third portion of a string of characters based on the generated matrix as disclosed in detail above. In step 718, registration device 2 stores the string of characters in association with the obtained identification information in a database, e.g. in database 30 via communication with server 3 and/or in a database comprised by registration device 2.

Turning to FIG. 7B and thus to a verification process of verifying a drug package B (which may correspond to drug package A or which may be a different drug package not registered or registered at a different registration stage), for example performed by mobile device 4, in a step 721, mobile device 4 performs steps 711, optionally step 712, and steps 714 to 716 and/or 717 for drug package B to generate a first string of characters and optionally to obtain corresponding identification information of drug package B.

In step 722, mobile device 4 determines if the first string of characters obtained for drug package B is present in a database. For example, mobile device 4 may communicate with server 3 via communication path 34 and may cause server 3 to determine if the first string of characters obtained for drug package B is present in database 30. If the first string of characters is determined to be present in database 30, mobile device 4 outputs confirmation information, e.g. by displaying corresponding information on display 41 in step 723. Such confirmation message may on the one hand indicate that the drug package is not a counterfeit drug package. On the other hand, if the image of the at least part of the surface obtained in steps 711 and 721 is obtained based on part of the surface including or corresponding to at least part of a surface of a seal for sealing drug package A and/or drug package B, the confirmation message may further indicate that the seal has not been (illegally) opened before. This is because opening the seal after the corresponding package has been registered by employing steps 711 to 718 will result in damage to the seal which will with high likelihood cause a string of characters generated in step 721 to differ from a string of characters generated in steps 715 to 717. Therefore, if a string of characters generated in step 721 corresponds to a string of characters stored in the database, it can with a high likelihood be assumed that the seal has not been illegally opened.

If the first string of characters obtained for drug package B is determined to be not present in database 30, mobile device 4 generates (or causes server 3 to generate, this optionally being implicit in step 722) t first model strings of characters being variants of the first string of characters in step 724. For example, 10 first model strings of characters may be generated, each model string of characters representing respective heights of the part of the surface as perceived under a different lighting condition.

In a step 725, mobile device 4 obtains (or causes server 3 to obtain, this optionally being implicit in step 722) u second strings of characters present in the database, e.g. in database 30 that are similar to any one of the t first model strings of characters and/or the first string of characters. For example, 7 second strings of characters may be found in database 30, a distance of which to the first string of characters and/or the first model strings of characters (as described above) is below a predetermined threshold (an example of a first or second threshold as referred to herein).

In a step 726, mobile device 4 generates (or causes server 3 to generate, this optionally being implicit in step 722) v second model strings of characters being variants of the each one of the second model strings of characters. For example 10 second model strings of characters may be generated for each of the 7 second strings of characters.

In a step 727, mobile device 4 determines (or causes server 3 to determine, this optionally being implicit in step 722) whether or not a string of characters is present (among the u second strings of characters and/or the v second model strings of characters) in the database, e.g. in database 30, a distance of which to the first and/or the first model string is below a predefined threshold (an example of the third predefined threshold referred to herein).

For example, the first model string of characters and the 10 first model string of characters (11 strings of characters) may be compared to the second strings of characters and the respective corresponding second model strings of characters (77 strings of characters) to determine if a pair (one of the 11 strings of characters and one of the 77 strings of characters) of strings of characters is present in the database with a distance below a predefined threshold (the third predefined threshold disclosed herein).

In the affirmative case, if at least one string of characters is present among the u second strings of characters and the v second model strings of characters, a distance of which to the first and/or the first model string of characters is below a predefined threshold (the third predefined threshold), mobile device 4 outputs in step 728 the confirmation information.

In an exemplary embodiment, in the non-affirmative case, if no string of characters is determined to be present among the u second strings of characters and the v second model strings of characters in the database, a distance of which to the first and/or the first model string is below a predefined threshold, mobile device 4 outputs non-affirmative information, e.g. via display 41 (e.g. "drug package not confirmed").

Thus, a method according to the second aspect advantageously enables determining whether or not a drug package has been registered in a database and thereby enables verifying that a drug package is not counterfeit (if a corresponding string of characters is stored in the database) and, in case the image has been obtained based at least in part on at least part of a surface of the seal, that the seal has not been opened and/or illegally manipulated.

The following example embodiments of the invention are also disclosed:

Embodiment 1 a. A method performed by at least one first apparatus, the method comprising:
b. obtaining or causing obtaining an image of at least a part of a surface of a sealed unit;
c. deriving or causing deriving a representation of the at least a part of the surface from the image, the representation comprising a set of values respectively representing a corresponding set of height levels of corresponding sections of the at least a part of the surface;
d. generating or causing generating a string of characters based on the representation of the at least a part of the surface, the string of characters comprising at least a first portion representative of the set of height levels of the corresponding sections of the at least a part of the surface and a second portion generated based on a function of the representation and/or of the first portion of the string of characters;
e. associating or causing associating information representing the string of characters with identification information of the sealed unit.

Embodiment 2 a. The method according to embodiment 1, further comprising:
b. obtaining or causing obtaining the identification information of the sealed unit from the sealed unit and/or via user input.

Embodiment 3 a. The method according to any of embodiments 1 to 2, wherein obtaining an image of at least a part of the surface of the sealed unit comprises at least one of:
b. obtaining or causing obtaining the image via a digital camera or scanner comprised by or connected to the at least one first apparatus;
c. obtaining or causing obtaining the image via a communication path from an external network device.

Embodiment 4 a. The method according to any of embodiments 1 to 3, wherein the height levels of the sections are representative of a microstructure of the surface of the sealed unit.

Embodiment 5 a. The method according to any of embodiments 1 to 4, wherein deriving the representation corresponds to or comprises:

b. converting or causing converting the image into a two-dimensional matrix, in particular where each dimension of the matrix corresponds to a spatial dimension of the image and wherein each entry of the matrix is a value representing a height of a corresponding section of the image.

Embodiment 6 a. The method according to any of embodiments 1 to 5, wherein the at least one first apparatus corresponds to or is comprised by a mobile device, by one or more network servers and/or by a server cloud.

Embodiment 7 a. The method according to any of embodiments 1 to 6, wherein the database is comprised by the at least one first apparatus and/or is connected to the at least one first apparatus via a communication path.

Embodiment 8 a. The method according to any of embodiments 1 to 7, wherein associating the information representing the string of characters with the identification information comprises at least one of the following:
b. storing or causing storing the information representing the string of characters with the identification information of the sealed unit;
c. providing or causing providing the information representing the string of characters in association with the identification information of the sealed unit to be accessible by at least one external network device, in particular via a communication path.

Embodiment 9 a. A method performed by at least one second apparatus, the method comprising:
b. obtaining or causing obtaining first information representing a first string of characters with a first portion representative of a set of height levels of corresponding sections of at least a part of a surface of a first sealed unit;
c. determining or causing determining, based on the obtained first information, whether or not the first string of characters is present in a database;
d. if the first string of characters is present in the database:
e. outputting or causing outputting confirmation information.

Embodiment 10 a. The method according to embodiment 9, wherein determining, based on the obtained first information, whether or not the first string of characters is present in a database comprises:
b. determining or causing determining, based on the obtained first information, whether or not the first string of characters is present in a database via communication with an external network device, in particular one or more servers and/or a server cloud, comprising or connected to the database.

Embodiment 11 a. The method according to any of embodiments 9 to 10, wherein determining, based on the obtained first information, whether or not the first string of characters is present in a database comprises:
b. determining or causing determining, based on the obtained first information, whether or not the first string of characters is stored in the database in association with identification information of the first sealed unit.

Embodiment 12 a. The method according to any of embodiments 9 to 11 further comprising:
b. obtaining or causing obtaining the identification information of the first sealed unit from the sealed unit, in particular via a camera and/or the scanner comprised by the at least one second apparatus and/or via user input.

Embodiment 13 a. The method according to any of embodiments 9 to 12, wherein the database is comprised by the at least one second apparatus and/or is connected to the at least one second apparatus via a communication path.

Embodiment 14 a. The method according to any of embodiment 1 to 13, wherein the database is a storage accessible via the communication path, in particular a storage comprised by or connected to a network server and/or a network server cloud.

Embodiment 15 a. The method according to any of claims 9 to 14, further comprising:
b. if the first string of characters is not present in the database:
c. determining or causing determining, based on a metric function, whether or not at least one second string of characters is present in the database, a distance of which to the first string of characters is below a first predefined threshold; and
d. outputting or causing outputting the confirmation information if at least one second string of characters is present in the database, the distance of which to the first string of characters is below the first predefined threshold.

Embodiment 16 a. The method according to any of embodiments 1 to 15, wherein the part of the surface of the sealed unit and/or of the first sealed unit corresponds to or comprises at least in part at least one of:
b. a bare surface portion of the sealed unit;
c. at least a part of a label of the sealed unit;
d. at least a part of a seal for sealing the sealed unit.

Embodiment 17 a. The method according to any of embodiments 9 to 16, further comprising:
b. if the first string of characters is not present in the database, the method further comprises the following steps (a), (b), and (c):
    i. obtaining or causing obtaining at least second information representing at least one first model string of characters with a first portion representative of a first model set of height levels of the corresponding sections of the at least a part of the surface of the first sealed unit;
ii. determining or causing determining, based on a metric function, whether or not at least one second string of characters is present in the database, a distance of which to the at least one first model string of characters and/or the first string of characters is below a second predefined threshold;
iii. outputting or causing outputting the confirmation information if at least one second string of characters is present in the database, the distance of which to the at least one first model string of characters and/or the first string of characters is below the second predefined threshold.

Embodiment 18 a. The method according to claim 17, further comprising:
b. if at least one second string of characters is determined to be present in the database, the at least one second string of characters comprising a first portion representative of a set of height levels of corresponding sections of at least a part of a surface of at least one respective second sealed unit corresponding to the at least one second string of characters and the distance of which to the first string of characters and/or to the at least one first model string of characters is below the first and/or the second predefined threshold, the method further comprises the following steps (a), (b) and (c):
i. obtaining or causing obtaining, for each one of the at least one second string of characters, at least third information representing at least one respective second model string of characters corresponding to the at least one second string of characters with a first portion being representative of a second model set of height levels of corresponding sections of at least a part of the surface of the respective second sealed unit corresponding to the at least one second string of characters;
ii. determining or causing determining whether or not at least one string of characters of the at least one second string of characters and the at least one corresponding second model string of characters is present in the database for which a distance to any one of the first string of characters and/or the at least one first model string of characters is below a third predefined threshold; and
iii. if at least one string of characters of the at least one second string of characters and the at least one corresponding second model string of characters is found, the distance of which to any one of the first string of characters and/or the at least one first model string of characters is below the third predefined threshold, outputting or causing outputting the confirmation information.

Embodiment 19 a. The method according to any of embodiments 9 to 18, wherein outputting the confirmation information corresponds to or comprises at least one of:
b. outputting or causing outputting a control signal configured for causing an external apparatus to perform a predetermined operation;
c. outputting or causing outputting information verifying the first sealed unit, in particular via a display comprised by the at least one second apparatus.

Embodiment 20 a. The method according to any of embodiments 9 to 19,
b. wherein for each one of the at least one first model string of characters, the first model set of height levels of the corresponding sections of the at least a part of the surface of the first sealed unit is obtained by calculating the height levels of the corresponding sections assuming different lighting conditions; and/or
c. wherein for each one of the at least one second model string of characters, the second model set of height levels of the corresponding sections of the at least a part of the surface of the second sealed unit is obtained by calculating the height levels of the corresponding sections assuming different lighting conditions.

Embodiment 21 a. The method according to any of embodiments 9 to 20, wherein the first string of characters, the at least one second string of characters, the at least one first model string of characters and the at least one second model string of characters each comprise respective second portions; and wherein respective mutual distances between the first string of characters, the at least one second string of characters, the at least one first model string of characters and the at least one second model string of characters are determined based on the metric function and based on the respective second portions.

Embodiment 22 a. The method according to any of embodiments 9 to 21, wherein obtaining the first information comprises:
b. obtaining or causing obtaining an image of at least a part of a surface of the first sealed unit;
c. deriving or causing deriving a representation of the at least a part of the surface from the image, the representation comprising a set of values respectively representing a corresponding set of height levels of corresponding sections of the at least a part of the surface;
d. generating or causing generating the first string of characters based on the representation of the at least a part of the surface;
e. or
f. receiving or causing receiving the first information via the communication path.

Embodiment 23 a. The method according to claim 22, wherein a second portion of the first string of characters is generated based on a function of the representation and/or of the first portion of the first string of characters.

Embodiment 24 a. The method according to any of embodiments 1 to 23, wherein obtaining the image of the at least a part of the surface comprises:
b. applying or causing applying ultraviolet, UV, infrared, IR, and/or white light to the at least a part of the surface.

Embodiment 25 a. The method according to any of embodiments 1 to 24, wherein the string of characters, the first string of characters, the second string of characters, the at least one first model string of characters, and/or the second model string of characters further comprises a third portion different from the first and/or the second portion and being determined based on a hash function of the first portion and/or the second portion and/or comprising a checksum of the first portion and/or the second portion.

Embodiment 26 a. The method according to any of embodiments 9 to 25, wherein the third predefined threshold corresponds to (and/or is equal to) the second predefined threshold and/or the first predefined threshold.

Embodiment 27 a. The method according to any of embodiments 1 to 26, wherein a mobile device corresponds to and/or is comprised by an Internet-of-Things (IoT) device, a smartphone, a tablet computer, a notebook computer, a smart watch, and a smart band.

Embodiment 28 a. The method according to any of embodiments 1 to 27, wherein height levels represent a microstructure of the at least part of the surface.

Embodiment 29 a. The method according to any of embodiments 1 to 28, wherein a communication path corresponds to and/or comprises is a (bi-directional) wireless and/or wired network connection, in particular a wireless network connection that enables a network entity to transmit and receive data via said connection.

Embodiment 30 a. The method according to embodiment 29, wherein a wireless connection comprises a wireless communication path or link in a wireless communication network, in particular a terrestrial wireless communication network like a Wireless Local Area Network (WLAN) or a cellular network, wherein WLAN is for example specified by the standards of the IEEE 802.11 family (http://www.ieee.org/) and wherein a cellular network may for example be a mobile phone network like a 2G/3G/4G/5G cellular communication network, the 2G/3G/4G/5G cellular radio communication standards being developed by the 3GPP and being available under http://www.3gpp.org/, wherein a wireless connection may further comprise a Device-to-Device (D2D) communication path.

Embodiment 31 a. The method according to any of embodiments 1 to 30, wherein the external network device corresponds to or comprises a network server and/or a network server cloud.

Embodiment 32 a. The method according to any of embodiments 1 to 31, wherein the sealed unit corresponds to or comprises at least one of:
b. a sealed package for one or more pharmaceutical products;
c. a sealed package for one or more medical tools;
d. a sealed bottle, in particular for an alcoholic beverage;
e. or a sealed package for a tobacco and/or nicotine based product, in particular for loose tobacco, one or more cigarettes, one or more cigars, and/or e-cigarette liquid;
f. a sealed consignment unit.

Embodiment 33 a. The method according to embodiment 32, wherein a seal for sealing the sealed bottle and/or the sealed package for the tobacco and/or nicotine based product corresponds to or comprises a tax stamp.

Embodiment 34 a. The method according to any of embodiments 32 or 33, wherein the identification information corresponds to or comprises at least one of:
a serial number, an origin of the pharmaceutical product and/or the medical tool, a batch number of the pharmaceutical product and/or the medical tool, a type of the pharmaceutical product and/or the medical tool, an identification number and/or code of the pharmaceutical product and/or the medical tool, a name of the pharmaceutical product and/or the medical tool, an expiration date of the pharmaceutical product, and/or information identifying an addressee of the pharmaceutical product and/or the medical tool, e.g. a name of the addressee, a place of birth of the addressee, date of birth of the addressee and/or residence of the addressee;
a serial number, an origin of the sealed bottle and/or the sealed package for the tobacco and/or nicotine based product, a batch number of the sealed bottle and/or the sealed package for the tobacco and/or nicotine based product, a type of the sealed bottle and/or the sealed package for the tobacco and/or nicotine based product, an identification number and/or code of the sealed bottle and/or the sealed package for the tobacco and/or nicotine based product, a name of the sealed bottle and/or the sealed package for the tobacco and/or nicotine based product, an expiration date of the sealed bottle and/or the sealed package for the tobacco and/or nicotine based product, and/or information identifying an addressee of the sealed bottle and/or the sealed package for the tobacco and/or nicotine based product, e.g. name and address of a customer with the intention to resell the sealed bottle and/or the sealed package for the tobacco and/or nicotine based product. As in the case of the above disclose pharmaceutical product, it becomes possible not only to verify activation, validity and/or authenticity of a tax stamp, it becomes in addition possible to identify, trace and track a corresponding sealed bottle and/or the sealed package for the tobacco and/or nicotine based product.

Embodiment 35 a. The method according to embodiment 34, wherein the identification information corresponds to or comprises identification information of an origin of the sealed consignment unit, a destination address of the sealed consignment unit, identification information of goods carried by the consignment unit, a serial number of an item carried by the consignment unit and/or a parameter characteristic of a physical property (e.g. weight, size and/or volume) of one or more items carried by the consignment unit.

Embodiment 36 a. An apparatus comprising at least one processor and at least one memory that contains program code, wherein the memory and the program code are configured to use the at least one processor to cause an apparatus to perform and/or control at least the method of any of embodiments 1 to 8.

Embodiment 37 a. An apparatus comprising at least one processor and at least one memory that contains program code, wherein the memory and the program code are configured to use the at least one processor to cause an apparatus to perform and/or control at least the method of any of embodiments 9 to 35.

Embodiment 38 a. System comprising at least one first apparatus configured to perform the method according to any of embodiments 1 to 8 and at least one second apparatus configured to perform the method according to any of embodiments 9 to 35.

In the specification, any presented connection in the described embodiments is to be understood in a way that the involved components are operationally coupled. Thus, the connections can be direct or indirect with any number or combination of intervening elements, and there may be merely a functional relationship between the components.

Moreover, any of the methods, processes and actions described or illustrated herein may be implemented using executable instructions in a general-purpose or special-purpose processor and stored on a computer-readable storage medium (e.g., disk, memory, or the like) to be executed by such a processor. References to a 'computer-readable storage medium' should be understood to encompass specialized circuits such as FPGAs, ASICs, signal processing devices, and other devices.

The expression "A and/or B" is considered to comprise any one of the following three scenarios: (i) A, (ii) B, (iii) A and B. Furthermore, the article "a" is not to be understood as "one", i.e. use of the expression "an element" does not preclude that also further elements are present. The term "comprising" is to be understood in an open sense, i.e. in a way that an object that "comprises an element A" may also comprise further elements in addition to element A.

It will be understood that all presented embodiments are only exemplary, and that any feature presented for a particular example embodiment may be used with any aspect of the invention on its own or in combination with any feature presented for the same or another particular example embodiment and/or in combination with any other feature not mentioned. In particular, the example embodiments presented in this specification shall also be understood to be disclosed in all possible combinations with each other, as far as it is technically reasonable and the example embodiments are not alternatives with respect to each other. It will further be understood that any feature presented for an example embodiment in a particular category (method/apparatus/computer program) may also be used in a corresponding manner in an example embodiment of any other category. It should also be understood that presence of a feature in the presented example embodiments shall not necessarily mean that this feature forms an essential feature of the invention and cannot be omitted or substituted.

The sequence of all method steps presented above is not mandatory, also alternative sequences may be possible. Nevertheless, the specific sequence of method steps exemplarily shown in the figures shall be considered as one possible sequence of method steps for the respective embodiment described by the respective figure.

The invention has been described above by means of example embodiments. It should be noted that there are alternative ways and variations which are obvious to a skilled person in the art and can be implemented without deviating from the scope of the appended claims.

What is claimed:

1. An apparatus comprising at least one processor and at least one memory including computer program code, the at least one memory and the computer program code configured to, with the at least one processor, cause an apparatus at least to perform or control:
   obtaining or causing obtaining an image of at least a part of a surface of a sealed unit;
   deriving or causing deriving a representation of the at least a part of the surface from the image, the representation comprising a set of values respectively representing a corresponding set of height levels of corresponding sections of the at least a part of the surface;
   generating or causing generating a string of characters based on the representation of the at least a part of the surface, the string of characters comprising at least a first portion representative of the set of height levels of the corresponding sections of the at least a part of the surface and a second portion generated based on a function of the representation and/or of the first portion of the string of characters, wherein the function is a most-recurring function and/or an averaging function; and
   associating or causing associating information representing the string of characters with identification information of the sealed unit.

2. The apparatus according to claim 1, wherein associating the information representing the string of characters with the identification information comprises at least one of the following:
   storing or causing storing the information representing the string of characters with the identification information of the sealed unit;
   providing or causing providing the information representing the string of characters in association with the identification information of the sealed unit to be accessible by at least one external network device, in particular via a communication path.

3. The apparatus according to claim 1, wherein obtaining the image comprises obtaining or causing obtaining the image of at least a part of:
   a bare surface portion of the sealed unit;
   a part of a label of the sealed unit;
   a part of a seal for sealing the sealed unit.

4. The apparatus according to claim 3, wherein obtaining the image of the at least a part of the surface comprises:

applying or causing applying ultraviolet, UV, infrared, IR, and/or white light to the at least a part of the surface.

5. An apparatus comprising at least one processor and at least one memory including computer program code, the at least one memory and the computer program code configured to, with the at least one processor, cause an apparatus at least to perform or control:
obtaining or causing obtaining first information representing a first string of characters with a first portion representative of a set of height levels of corresponding sections of at least a part of a surface of a first sealed unit;
determining or causing determining, based on the obtained first information, whether or not the first string of characters is present in a database; and
if the first string of characters is present in the database:
outputting or causing outputting confirmation information;
if the first string of characters is not present in the database:
determining or causing determining, based on a metric function, whether or not at least one second string of characters is present in the database, a distance of which to the first string of characters is below a first predefined threshold; and
outputting or causing outputting the confirmation information if at least one second string of characters is present in the database, the distance of which to the first string of characters is below the first predefined threshold.

6. The apparatus according to claim 5, wherein the part of the surface of the sealed unit and/or of the first sealed unit corresponds to or comprises at least in part at least one of:
a bare surface portion of the sealed unit;
at least a part of a label of the sealed unit;
at least a part of a seal for sealing the sealed unit.

7. The apparatus according to claim 5, wherein the at least one memory and the computer program code are further configured to, with the at least one processor, cause the apparatus at least to perform or control:
if the first string of characters is not present in the database, the method further comprises the following steps (a), (b), and (c):
(a) obtaining or causing obtaining at least second information representing at least one first model string of characters with a first portion representative of a first model set of height levels of the corresponding sections of the at least a part of the surface of the first sealed unit;
(b) determining or causing determining, based on a metric function, whether or not at least one second string of characters is present in the database, a distance of which to the at least one first model string of characters and/or the first string of characters is below a second predefined threshold;
(c) outputting or causing outputting the confirmation information if at least one second string of characters is present in the database, the distance of which to the at least one first model string of characters and/or the first string of characters is below the second predefined threshold.

8. The apparatus according to claim 7, wherein the at least one memory and the computer program code are further configured to, with the at least one processor, cause the apparatus at least to perform or control:
if at least one second string of characters is determined to be present in the database, the at least one second string of characters comprising a first portion representative of a set of height levels of corresponding sections of at least a part of a surface of at least one respective second sealed unit corresponding to the at least one second string of characters and the distance of which to the first string of characters and/or to the at least one first model string of characters is below the first and/or the second predefined threshold, the method further comprises the following steps (a), (b) and (c):
(a) obtaining or causing obtaining, for each one of the at least one second string of characters, at least third information representing at least one respective second model string of characters corresponding to the at least one second string of characters with a first portion being representative of a second model set of height levels of corresponding sections of at least a part of the surface of the respective second sealed unit corresponding to the at least one second string of characters;
(b) determining or causing determining whether or not at least one string of characters of the at least one second string of characters and the at least one corresponding second model string of characters is present in the database for which a distance to any one of the first string of characters and/or the at least one first model string of characters is below a third predefined threshold; and
(c) if at least one string of characters of the at least one second string of characters and the at least one corresponding second model string of characters is found, the distance of which to any one of the first string of characters and/or the at least one first model string of characters is below the third predefined threshold, outputting or causing outputting the confirmation information.

9. The apparatus according to claim 5,
wherein for each one of the at least one first model string of characters, the first model set of height levels of the corresponding sections of the at least a part of the surface of the first sealed unit is obtained by calculating the height levels of the corresponding sections assuming different lighting conditions; and/or
wherein for each one of the at least one second model string of characters, the second model set of height levels of the corresponding sections of the at least a part of the surface of the second sealed unit is obtained by calculating the height levels of the corresponding sections assuming different lighting conditions.

10. The apparatus according to claim 5, wherein the first string of characters, the at least one second string of characters, the at least one first model string of characters and the at least one second model string of characters each comprise respective second portions; and wherein respective mutual distances between the first string of characters, the at least one second string of characters, the at least one first model string of characters and the at least one second model string of characters are determined based on the metric function and based on the respective second portions.

11. The apparatus according to claim 5, wherein obtaining the first information comprises:
obtaining or causing obtaining an image of at least a part of a surface of the first sealed unit;
deriving or causing deriving a representation of the at least a part of the surface from the image, the representation comprising a set of values respectively representing a corresponding set of height levels of corresponding sections of the at least a part of the surface;

generating or causing generating the first string of characters based on the representation of the at least a part of the surface;
or
receiving or causing receiving the first information via a network connection.

12. The apparatus according to claim 11, wherein a second portion of the first string of characters is generated based on a function of the representation and/or of the first portion of the first string of characters.

13. The apparatus according to claim 5, wherein obtaining the image comprises obtaining or causing obtaining the image of at least a part of:
a bare surface portion of the sealed unit;
a part of a label of the sealed unit;
a part of a seal for sealing the sealed unit.

14. The apparatus according to claim 13, wherein obtaining the image of the at least a part of the surface comprises:
applying or causing applying ultraviolet, UV, infrared, IR, and/or white light to the at least a part of the surface.

15. The apparatus according to claim 5, wherein the string of characters, the first string of characters, the second string of characters, the at least one first model string of characters, and/or the second model string of characters further comprises a third portion different from the first and/or the second portion and being determined based on a hash function of the first portion and/or the second portion and/or comprising a checksum of the first portion and/or the second portion.

16. A method performed by at least one apparatus, the method comprising:
obtaining or causing obtaining first information representing a first string of characters with a first portion representative of a set of height levels of corresponding sections of at least a part of a surface of a first sealed unit;
determining or causing determining, based on the obtained first information, whether or not the first string of characters is present in a database; and
if the first string of characters is present in the database:
outputting or causing outputting confirmation information;
if the first string of characters is not present in the database:
determining or causing determining, based on a metric function, whether or not at least one second string of characters is present in the database, a distance of which to the first string of characters is below a first predefined threshold; and
outputting or causing outputting the confirmation information if at least one second string of characters is present in the database, the distance of which to the first string of characters is below the first predefined threshold.

17. The method according to claim 16, wherein the part of the surface of the sealed unit and/or of the first sealed unit corresponds to or comprises at least in part at least one of:
a bare surface portion of the sealed unit;
at least a part of a label of the sealed unit;
at least a part of a seal for sealing the sealed unit.

18. The method according to claim 16, further comprising:
if the first string of characters is not present in the database, the method further comprises the following steps (a), (b), and (c):
(a) obtaining or causing obtaining at least second information representing at least one first model string of characters with a first portion representative of a first model set of height levels of the corresponding sections of the at least a part of the surface of the first sealed unit;
(b) determining or causing determining, based on a metric function, whether or not at least one second string of characters is present in the database, a distance of which to the at least one first model string of characters and/or the first string of characters is below a second predefined threshold;
(c) outputting or causing outputting the confirmation information if at least one second string of characters is present in the database, the distance of which to the at least one first model string of characters and/or the first string of characters is below the second predefined threshold.

19. The method according to claim 18, further comprising:
if at least one second string of characters is determined to be present in the database, the at least one second string of characters comprising a first portion representative of a set of height levels of corresponding sections of at least a part of a surface of at least one respective second sealed unit corresponding to the at least one second string of characters and the distance of which to the first string of characters and/or to the at least one first model string of characters is below the first and/or the second predefined threshold, the method further comprises the following steps (a), (b) and (c):
(a) obtaining or causing obtaining, for each one of the at least one second string of characters, at least third information representing at least one respective second model string of characters corresponding to the at least one second string of characters with a first portion being representative of a second model set of height levels of corresponding sections of at least a part of the surface of the respective second sealed unit corresponding to the at least one second string of characters;
(b) determining or causing determining whether or not at least one string of characters of the at least one second string of characters and the at least one corresponding second model string of characters is present in the database for which a distance to any one of the first string of characters and/or the at least one first model string of characters is below a third predefined threshold; and
(c) if at least one string of characters of the at least one second string of characters and the at least one corresponding second model string of characters is found, the distance of which to any one of the first string of characters and/or the at least one first model string of characters is below the third predefined threshold, outputting or causing outputting the confirmation information.

20. A non-transitory computer readable storage medium in which a computer program is stored, the computer program when executed by a processor causing an apparatus or system to perform or control:
obtaining or causing obtaining first information representing a first string of characters with a first portion representative of a set of height levels of corresponding sections of at least a part of a surface of a first sealed unit;
determining or causing determining, based on the obtained first information, whether or not the first string of characters is present in a database; and if the first string of characters is present in the database:
outputting or causing outputting confirmation information;
if the first string of characters is not present in the database:
determining or causing determining, based on a metric function, whether or not at least one second string of characters is present in the database, a distance of which to the first string of characters is below a first predefined threshold; and
outputting or causing outputting the confirmation information if at least one second string of characters is present in the database, the distance of which to the first string of characters is below the first predefined threshold.

21. A method performed by at least one apparatus, the method comprising:
obtaining or causing obtaining an image of at least a part of a surface of a sealed unit;
deriving or causing deriving a representation of the at least a part of the surface from the image, the representation comprising a set of values respectively representing a corresponding set of height levels of corresponding sections of the at least a part of the surface;
generating or causing generating a string of characters based on the representation of the at least a part of the surface, the string of characters comprising at least a first portion representative of the set of height levels of the corresponding sections of the at least a part of the surface and a second portion generated based on a function of the representation and/or of the first portion of the string of characters, wherein the function is a most-recurring function and/or an averaging function; and
associating or causing associating information representing the string of characters with identification information of the sealed unit.

22. A non-transitory computer readable storage medium in which a computer program is stored, the computer program when executed by a processor causing an apparatus or system to perform or control:
obtaining or causing obtaining an image of at least a part of a surface of a sealed unit;
deriving or causing deriving a representation of the at least a part of the surface from the image, the representation comprising a set of values respectively representing a corresponding set of height levels of corresponding sections of the at least a part of the surface;
generating or causing generating a string of characters based on the representation of the at least a part of the surface, the string of characters comprising at least a first portion representative of the set of height levels of the corresponding sections of the at least a part of the surface and a second portion generated based on a function of the representation and/or of the first portion of the string of characters, wherein the function is a most-recurring function and/or an averaging function; and
associating or causing associating information representing the string of characters with identification information of the sealed unit.

23. A system, comprising:
at least one apparatus comprising at least one processor and at least one memory including computer program code, the at least one memory and the computer program code configured to, with the at least one processor, cause an apparatus at least to perform or control:
obtaining or causing obtaining an image of at least a part of a surface of a first sealed unit;
deriving or causing deriving a representation of the at least a part of the surface from the image, the representation comprising a set of values respectively representing a corresponding set of height levels of corresponding sections of the at least a part of the surface;
generating or causing generating a first string of characters based on the representation of the at least a part of the surface, the first string of characters comprising at least a first portion representative of the set of height levels of the corresponding sections of the at least a part of the surface and a second portion generated based on a function of the representation and/or of the first portion of the string of characters; and
associating or causing associating first information representing the first string of characters with identification information of the first sealed unit; and
at least one apparatus comprising at least one processor and at least one memory including computer program code, the at least one memory and the computer program code configured to, with the at least one processor, cause an apparatus at least to perform or control:
obtaining or causing obtaining first information representing a first string of characters with a first portion representative of a set of height levels of corresponding sections of at least a part of a surface of a first sealed unit;
determining or causing determining, based on the obtained first information, whether or not the first string of characters is present in a database; and
if the first string of characters is present in the database:
outputting or causing outputting confirmation information;
if the first string of characters is not present in the database:
determining or causing determining, based on a metric function, whether or not at least one second string of characters is present in the database, a distance of which to the first string of characters is below a first predefined threshold; and
outputting or causing outputting the confirmation information if at least one second string of characters is present in the database, the distance of which to the first string of characters is below the first predefined threshold.

* * * * *